(12) United States Patent
Vojdani

(10) Patent No.: US 6,858,398 B2
(45) Date of Patent: Feb. 22, 2005

(54) SALIVA TEST FOR DETECTION OF FOOD ALLERGY AND INTOLERANCE

(75) Inventor: Aristo Vojdani, Los Angeles, CA (US)

(73) Assignee: Immunosciences Lab., Inc., Beverly Hills, CA (US)

( * ) Notice: Subject to any disclaimer, the term of this patent is extended or adjusted under 35 U.S.C. 154(b) by 252 days.

(21) Appl. No.: 10/156,333

(22) Filed: May 24, 2002

(65) Prior Publication Data

US 2003/0143627 A1 Jul. 31, 2003

Related U.S. Application Data

(63) Continuation-in-part of application No. 09/930,785, filed on Aug. 14, 2001, now Pat. No. 6,689,569.
(51) Int. Cl.$^7$ ...................... G01N 33/53; G01N 33/567; G01N 33/569; G01N 33/566
(52) U.S. Cl. ...................... 435/7.2; 435/7.31; 435/7.33; 435/7.34; 435/7.35; 435/7.37; 436/501
(58) Field of Search ................................ 435/7.2, 7.31, 435/7.33, 7.34, 7.35, 7.37, 7.1; 436/501

(56) References Cited

PUBLICATIONS

Kolmannskog et al (Int. Archs Allergy appl. Immun. 76: 133–137, 1985).*

J.A. Anderson, "The Establishment of Common Language Concerning Adverse Reactions to Foods and Food Additives", *J. Allergy Clin Immunol* Jul., 1986, vol. 78, pp. 140–144.

N.E. Eriksson, "Food Sensitivity Reported by Patients with Asthma and Hay Fever," *Allergy*, 33: 189–196 (1978).

A.E. Sloan, et al., "A Perspective on Popular Perceptions of Adverse Reactions to Foods," *J. Allergy Clin Immunol.*, vol. 78, ™1, Pt 2, pp. 127–133.

H.A. Sampson, et al. (editors), Immediate Reactions to Foods *Food Allergy Adverse Reactions to Foods and Food Additives*, Oxford, 1991, Blackwell Scientific Publications.

Luisa Businco, et al., "Chronic Diarrhea Due to Cow's Milk Allergy. A 4– to 10–Year Follow Up Study" *Annals of Allergy*, vol. 55, Dec. 1985, pp. 844–847.

A. Dannaeus, et al., "A Follow–Up Study of Infants With Adverse Reactions to Cow's Milk I. Serum IgE, Skin Test Reactions and RAST in Relation to Clinical Course", *Acta Pediatr Scand*, vol. 68, pp. 377–382 (1979).

T. Kohno, et al., "Antibodies to Food Antigens in Japanese Patients with Type 1 Diabetes Mellitus," *Diabetes Research & Clinical Practice*, vol. 55 (2002) 1–9.

H. Kiyono, et al., "The Mucosal Immune System: From Specialized Immune Defense to Inflammation and Allergy," *ACTA Odontol Scan*, vol. 59 (2001) pp. 145–153.

M. Kanda, et al., "Detection and Rapid Increase of Salivary Antibodies to *Staphylococcus Lentus*, and Indigenous Bacterium in Rabbit Saliva, Through a Single Tonsillar Application of Bacterial Cells," *Oral Microbiol Immunol*, vol. 16 (2001) pp. 257–264.

M. Plante, et al., "Nasal Immunization With Subunit Proteosome Influenza Vaccines Induces Serum HAI, Mucosal IgA and Protection Against Influenza Challenge," *Vaccine*, vol. 20 (2002) pp. 218–225.

S.C. Kraft, et al., "Gastric Acid Output and Circulating Anti–Bovine Serum Albumin in Adults," *Clin. Exp. Immunol.* (1967) vol. 2, pp. 321–330.

M.F. Kagnoff, "Effects of Antigen–Feeding on Intestinal and Systemic Immune Responses," *J. Immunol.* vol. 120, No. 2, Feb. 1978, pp. 395–399.

B. de Montrion, et al., "Études Des Immunoglobulines Salivaires Après Vaccination Locale Antistreptococcique," *Patholoogie–Biologie*, Apr. 1974, pp. 305–312 (French version—no translation attached).

J.R. McGhee, et al., "Effective Immunity to Dental Caries: Protection of Gnotobiotic Rats by Local Immunization With Streptococcus Mutants," *J. Immunol.* vol. 114, No. 1, Pt. 2, Jan. 1975, pp. 300–305.

B. Krasse, et al., "Antibodies Reacting With *Streptococcus Mutans* In Secretions From Minor Salivary Glands–in Humans,", *Adv. Exp. Med. Biol.* 107:349–354, 1978.

A. Husband, et al., "The Origin and Antigen–Dependent Distribution of IgA–Containing Cells in the Intestine," *J. Exp. Med.* 148: 1146–1160, (1978).

R. Clements, "Fruit Proteins: Extraction and Electrophoresis," *Analytical Biochemistry* 13, 390–401 (1965).

M. Bradford, "A Rapid and Sensitive Method for the Quantitation of Microgram Quantities of Protein Utilizing the Principle of Protein–Dye Binding," *Anal. Biochem*, vol. 72, (1976) pp. 248–254.

H. Steinhart, "Introducing Allergists to Food Chemistry," *Allergy*, vol. 56 (2001) Supp. 67, pp. 9–11.

C. Ortolani, et al., "Introducing Chemists to Food Allergy," *Allergy*, 2001, vol. 56, Suppl. 67 (2001) pp. 5–8.

(List continued on next page.)

*Primary Examiner*—Mark Navarro
(74) *Attorney, Agent, or Firm*—Knobbe, Martens, Olson & Bear LLP

(57) ABSTRACT

A method for determining the presence of food allergy or food intolerance and their cross-reactive tissue antigens is disclosed. The method includes determining a level of antibodies against a dietary antigen in a mucosal sample from the patient and comparing the level with normal levels of the antibodies. Dietary antigens that were tested include milk and milk products; eggs and egg products; meat and meat products; fish, mollusks, and crustaceans and their products; oils, fats, and their products; grains and grain products; pulses, seed, kernels, nuts, and their products; vegetable and vegetable products; fruit and fruit products; sugar, sugar product, chocolate products, and confectionary; and spices.

21 Claims, 12 Drawing Sheets

OTHER PUBLICATIONS

D. Barnett, et al., "Multiplicity of Allergens in Peanuts," *J. Allergy Clin. Immunol.* vol. 72, №1, Jul., 1983, pp. 61–68.

K. Aas, et al., "Studies of Hypersensitivity to Fish: Partial Purification and Crystallization of a Major Allergenic Component of Cod," *Int. Arch. Allergy,* vol. 32 (1967), pp. 1–20.

H. Izumi, "Nucleotide Sequence of a cDNA Clone Encoding a Major Allergenic Protein in Rice Seeds," *Fed. of Eurpean Biochem Societies,* vol. 302, №3, May 1992, pp. 213–216.

S. Elsayed, et al., "Immunochemical Analysis of Cod Fish Allergen M: Locations of the Immunoglobulin Binding Sites as Demonstrated by the Native and Synthetic Peptides," *Allergy,* (1983), vol. 38, pp. 449–459.

S. Nagpal, et al., Isolation and Characterization of Heat–Stable Allergens from Shrimp (*Penaeus Indicus*), *J. Allergy Clin. Immunol.,* Jan. 1989, vol. 83, №1, pp. 26–36.

P. Chatchatee, et al., "Identification of IgE and IgG Binding Epitopes on β– and k –casein in Cow's Milk Allergic Patients," *Clin. Exp. Allergy,* (2001), vol. 31, pp. 1256–1262.

K. Palosuo, et al., "Rye γ–70 and γ35 Secalins and Barley γ–3 Hordein Cross–React with ω5 Gliadin, a Major Allergen in Wheat–Dependent, Exercise–Induced Anaphylaxis," *Clin Exp. Allergy* vol. 31 (2001), pp. 466–473.

J. Wal, "Structure and Function of Milk Allergens," *Allergy,* 2001, vol. 56, Supp. 67: 35–38.

L. Poulsen, et al., "Allergens From Fish and Egg," *Allergy* (2001) vol. 56, Supp. 67, pp. 39–42.

S. Vieths, et al., "Optimized Allergen Extracts and Recombinant Allergens in Diagnostic Applications", *Allergy* (2001) vol. 56, Suppl. 67, pp. 78–82.

P.S.C. Leung, et al., "cDNA Cloning and Molecular Identification of the Major Oyster Allergen from the Pacific Oyster *Crassostrea gigas*," *Clin. Exp. Allergy,* (2001). vol. 31, pp. 1287–1294.

W.A. Walker, et al. "Intestinal Antibodies," *New England J. of Medicine.,* Oct. 6, 1977, vol. 297, No. 14, pp. 767–773.

S. Challacombe (editor), "The Induction of Secretory IgA Responses" in *Food Allergy and Intolerance* published by W.B. Sanders Eastboorne England, 1987.

J. Mestecky, et al., "Selective Induction of an Immune Response in Human External Secretions by Ingestion of Bacterial Antigen," *J. Clin Invest.,* vol. 61, Mar. 1978, pp. 731–737.

K. Zee, et al., "Salivary Immunoglobulin A Levels In Rapid and Slow Plaque Formers: A Pilot Study," *Microbios* 106 S2 81–87 (2001).

H. Kushimoto, et al., "Masked Type I Wheat Allergy," *Arch Dermatol,* vol. 121, Mar. 1985, pp. 355–360.

R. Enberg, "Food–Induced Oropharyngeal Systems, the Oral Allergy Syndrome," In Anderson JA, editor. *Food Allergy: Immunology and Allergy Clinics of North America* (vol. II), Philadelphia, 1991, WB Saunders.

A. Davies, "An Investigation Into the Serological Properties of Dysentery Stools," *The Lancet,* Nov. 11, 1922, pp. 1009–1012.

* cited by examiner

SALIVA TEST FOR DETECTION OF FOOD ALLERGY AND INTOLERANCE

CROSS-REFERENCES TO RELATED APPLICATIONS

This application is a continuation-in-part of patent application Ser. No. 09/930,785, filed Aug. 14, 2001 now U.S. Pat. No. 6,689,569.

BACKGROUND OF THE INVENTION

Food allergy has become a problem which concerns many clinicians. Adverse reactions to foods in which the pathogenesis involves an immunological response to food components are appropriately called food-hypersensitivity reactions. This term is considered to be synonymous with "food allergy" (1).

There are only limited data on the prevalence of food hypersensitivity in specific populations. The public's perception of the number of individuals affected by food allergies is far in excess of what can be demonstrated under controlled circumstances. One survey among adult atopic patients revealed that 24% claimed "allergic" symptoms on eating or handling various foods (2). Another survey indicated that concern among family members that one or more of them might have a food allergy made this fear the second most frequent cause of altering the family's dietary intake behind salt restriction for hypertension (3).

Immune-mediated adverse reactions to foods can be divided into distinct clinicopathologic entities based on presentation (immediate or delayed), target organ specificity, and pathogenic mechanisms. By far, the most common reactions are IgE mediated and dependent on activation of mast cells in specific tissues. Such reactions are immediate and in severe cases may be life-threatening. Allergic eosinophilic gastroenteritis in some instances also appears to be due to repeated and frequent IgE-mast cell-mediated reactions in the gastrointestinal mucosal. Food-induced colitis/enterocolitis is observed almost exclusively in infants and children and is not strictly IgE dependent. Finally, gluten-sensitive enteropathy (celiac sprue) and dermatitis herpetiformis are due to abnormal immune responses to gluten (gliadin) that are non-IgE related (4, 5).

Immediate reactions to foods can involve one or more target systems, including the skin, respiratory tract, gastrointestinal mucosal, and cardiovascular system. In a double-blind challenge, the first signs of a reaction usually are noted within minutes following ingestion of a food known to provoke such a reaction, and almost always within one hour. Careful clinical observation has made it possible to document that the signs and symptoms initially follow a pattern reflecting the sites of initial exposure to the incriminated food. Thus, oropharyngeal reactions are frequently reported first, followed by gastrointestinal responses, and then involvement of the skin and respiratory tract (6–7).

The constellation of oropharyngeal symptoms developing simultaneously with food ingestion is termed the oral allergy syndrome. It can occur in the absence of systemic symptoms. This pattern of reactivity to food is most commonly due to fruits and vegetables (7). Symptoms include pruritus, tingling, and angioedema of the lips. Throat tightness, facial flushing, oral mucosal blebs, and hoarseness are reported. The clinical diagnosis of an IgE-mediated immediate reaction to a specific food may be supported by skin testing or by measuring allergen-specific IgE by RAST or ELISA tests (8, 9).

Unlike the immediate effects of IgE-mediated allergy, the IgG and IgA-mediated food allergy and intolerance reactions can take several days to appear. Levels of IgG and IgA antibodies in the blood against different food antigens have been used for demonstration of delayed food allergy and intolerance reactions. Therefore, raised serum or plasma IgG and IgA levels of food-specific antibodies are often associated with food allergies. However, measurement of IgG or IgA in the blood may miss abnormal immune reaction to many food antigens (10–13). In one instance, it is known that oral or intragastric administration of dietary soluble proteins such as bovine gammaglobulin (BGG) and ovalbumin or eggalbumin results in salivary IgA production, but not in any antibody production in serum (14–16).

Manifestation of Antibodies

The deposition of antigens in the gut has been shown to lead to the production of IgA antibodies in secretion at sites distant from the gut, such as colostrums, lacrimal and salivary secretions in man and salivary secretions in rhesus monkeys and in rats (17–19).

A general conclusion, therefore, is that the secretory immune system can be stimulated centrally and that precursors of IgA-producing cells migrate from the gut-associated lymphoid tissue to several secretory sites in addition to the lamina propria of the gut itself. Therefore, if antigens are injected into the submucosal tissues, they are likely to induce serum IgG antibodies as well as secretory IgA antibodies in saliva. However, if it is applied topically to the skin or to the intraepiethelial tissue, secretory IgA is the main product, which is detected in saliva. The role of topically applied antigen in the localization and persistence of IgA responses has been demonstrated in several secretory sites, including the respiratory tract, oral cavity, gut and vagina (20–22).

The evidence that cells migrate from the gut to various secretory tissues, and that immunization in the gut leads to antibodies at various secretory sites has led to the concept of a common mucosal system. However, this concept may be an oversimplification, since although immunization in the lung may lead to antibodies in distant secretory sites, such as salivary glands, immunization in the lacrimal glands has also been shown to lead to the production of antibodies in saliva. Thus, with firm evidence that antigen deposition in the gut may lead to antibodies not only in the gut but also in saliva, lungs, lacrimal secretions and genitourinary tract, it is probably more correct to designate the system as an enteromucosal system (2, 3).

Saliva is a source of body fluid for detection of an immune response to bacterial, food, and other antigens present in the oral cavity and gastrointestinal tract. Indeed, salivary antibody induction has been widely used as a model system to study secretory responses to ingested material, primarily because saliva is an easy secretion to collect and analyze.

It seems to be a general feature that salivary IgA antibodies can be induced in a variety of species in the absence of serum antibodies. This has been demonstrated after immunization with particulate bacterial antigens in human could selectively induce an immune response to Streptococcus mutans by oral administration of the antigen. This route of administration resulted only in antibody production in saliva and not in serum. Similar mucosal immune response in the form of saliva IgA did occur in monkeys, rabbits, rats, and mice after oral administration of Streptococcus mutans, Staphylocuccus or different viral antigens and peptides (13, 14–23). The lack of production of IgG, but IgA production in saliva after oral or intragastric administration of bacterial antigens is shown in the following Table 1.

TABLE 1

Induction of salivary IgA antibodies after stimulation of gut-associated lymphoid tissue

| Species | Antigen | Route of Administration | Salivary IgA Production | Serum Antibody Production |
|---|---|---|---|---|
| Human | Streptococcus Mutans | Oral | ++ | − |
| Monkeys | Streptococcus Mutans | Intragastric | ++ | − |
| Rabbits | Penumococcus or BGG | Intragastric | ++ | − |
| Rats | Streptococcus or Mutans | Oral | ++ | − |
| Mice | Streptococcus Mutans or Ovalbumin | Intragastric | ++ | − |
| Mice | Viral Peptides | Nasal | ++ | − |

Secretory IgA is capable of functioning as a blocking antibody, which can create a barrier to certain macromolecules, bacteria, and viruses. The interaction with secretory IgA will not permit such antigens to interact with the mucosa and blocks their entrance and exposure to the gut-associated lymphoid tissue. This blockage permits the host to shield efficiently the systemic immune response, local immune response, or both, from being bombarded by many molecules.

The properties of human IgA in serum and saliva are completely different. Serum IgA is monomeric and contains 80–90% $IgA_1$ and 10–20% $IgA_2$ while secretory IgA is polymeric and contains 50–75% $IgA_1$ and 25–50% $IgA_2$.

Because of these properties, secretory IgA can bind to the invading organisms more effectively. Therefore, secretory IgA have anti-bacterial, anti-fungal, and anti-viral activities, and play an important role in protection of mucosal surfaces from adherence of microorganisms. This prevention of colonization of the mucous membrane by secretory IgA is done by binding and blocking of specific binding sites on the bacterial cell wall. A decrease in adherence results in enhanced clearance of the bacteria by oral secretion and immunological mechanisms. For this reason in patients with secretory IgA deficiency, frequent infections have been observed.

An additional role of secretory IgA is prevention of diffusion of food antigens into mucous membranes. Therefore, a secretory IgA deficient person is more exposed to high levels of antigens or allergens. This phenomenon, along with T-cell regulatory abnormalities which occurs in most patients with IgA deficiency, make them more prone to development of allergies and autoimmune diseases.

Despite the enteric route of exposure to food antigens and peptides, food-specific antibodies are measured only in blood, but not in saliva.

SUMMARY OF THE INVENTION

For the above reasons, saliva has been selected not only because of its relevance in disease, but mainly because it is an accessible fluid, easy to collect, and is thought to show representative responses in secretions after enteric or intragastric immunization. Disclosed herein is a method of measuring salivary IgA and IgM against different food antigens and peptides for use in determining food allergy and food intolerance.

A method for determining the presence of food allergy or food intolerance in a patient includes (a) determining a level of antibodies against a dietary antigen present in the food in a mucosal sample from the patient; and (b) comparing the level determined in step (a) with normal levels of the antibodies in said mucosal sample.

The possible outcomes for the comparison include (i) lower than normal levels or about normal levels of dietary antigen antibodies indicate optimal conditions; and (ii) higher than normal levels of dietary antigen antibodies indicate a food allergy or food intolerance.

In another embodiment, there is a method for determining a type of antibody in a presence of food allergy or food intolerance to a food in a patient, comprising (a) determining a level of antibodies against a dietary antigen present in the food in a first mucosal sample from the patient; (b) determining a level of antibodies against cross-reactive tissue antigen present in a second muscosal sample from the patient, wherein said first and second samples are the same or different; and (c) comparing the level of antibodies determined in steps a) and b) with normal levels of the antibodies.

The possible outcomes for the comparison include (i) about normal levels of antibodies against the dietary antigen and normal levels of antibodies against cross-reactive tissue antigen indicate optimal conditions; (ii) higher than normal levels of antibodies against the dietary antigen and about normal levels of antibodies against cross-reactive tissue antigen indicate food allergy and intolerance without cross-reacting to tissue antigens; (iii) about normal levels of antibodies against the dietary antigen and higher than normal levels of antibodies against cross-reactive tissue antigen indicate an autoimmune reaction not related to the dietary antigens; and (iv) higher than normal levels of antibodies against the dietary antigen and higher than normal levels of antibodies against cross-reactive tissue antigen indicate a presence of food allergy and intolerance resulting in an autoimmune reaction.

Further objects, features and other advantages of the preferred embodiments become apparent from the ensuing detailed description, considered together with the appended figures.

DETAILED DESCRIPTION OF THE PREFERRED EMBODIMENTS

Figure 1:
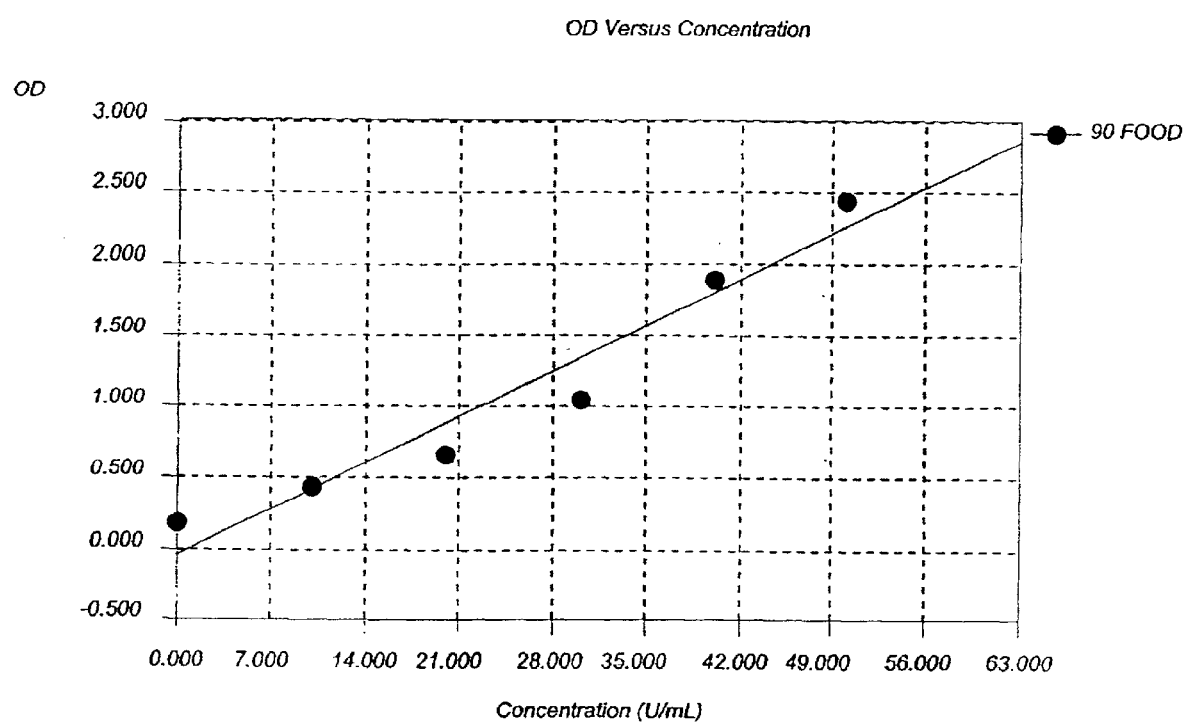
FIGS. 1–6 show calibration graphs of optical density for binding reactions versus concentration of food IgA.

A single test that will accurately inform a physician of clinical conditions used to diagnose patients who may suffer from food allergies or food intolerance has been developed. The test utilizes a test method that measures antibody titers to dietary antigens. The test can also utilize a test method that measures the antibodies' ability to bind to a recombinant antigen, synthetic peptide, a peptide prepared by enzymatic digestion corresponding to the dietary antigen, or different cross-reactive tissue antigens.

In order to assist the physician to make a more etiologic based diagnosis, we have developed an immunoassay for detecting food allergies and food intolerance in a patient using mucosal secretions. Mucosal secretions are secretions of a mucosa, such as saliva. Although saliva is mentioned throughout the disclosure, it is not meant to be limiting and can refer to any mucosal secretion.

The test involves using a method for detecting food allergies and food intolerance in a patient. The method includes (a) determining a level of antibodies against a dietary antigen in the food in a mucosal sample from a patient; and (b) comparing the level determined in step (a) with normal levels of the antibodies in said mucosal sample.

The possible outcomes for the comparison include (i) lower than normal or about normal levels of dietary antigen antibodies indicate optimal conditions; and (ii) higher than normal levels of dietary antigen antibodies indicate a food allergy or food intolerance.

As mentioned previously, food allergy has become a problem which concerns many clinicians. Adverse reactions to foods in which the pathogenesis involves an immunological response to food components are appropriately called food-hypersensitivity reactions. This term is considered to be synonymous with "food allergy". Food intolerance is an adverse reaction to food or food components which does not involve the immune system. Food intolerance can be caused by a metabolic reaction to an enzyme deficiency, such as the inability to digest milk properly; by food poisoning, such as ingesting contaminated or spoiled fish; or a food idiosyncrasy, such as sulfite-induced asthma.

Dietary antigens of the preferred embodiments are classified into the general groups as followed: milk and milk products; eggs and egg products; meat and meat products; fish, mollusks, and crustaceans and their products; oils, fats, and their products; grains and grain products; pulses, seeds, kernels, nuts, and their products; vegetables and vegetable products; fruits and fruit products; sugar, sugar products, chocolate products, and confectionary; and spices and herbs.

"Milk and milk products" include, but are not limited to, American cheese, cheddar cheese, cottage cheese, cow's milk, goat's milk, Swiss cheese, and yogurt.

"Eggs and egg products" include, but is not limited to, eggs.

"Meat and meat products" include, but are not limited to, beef, chicken, pork, and turkey.

"Fish, mollusks, and crustaceans and their products" include, but are not limited to, clam, codfish, crab, halibut, lobster, oyster, salmon, sardine, scallop, shrimp, sole, trout, and tuna.

"Oils, fats, and their products" include, but is not limited to, butter.

"Grains and grain products" include, but are not limited to, barley, buckwheat, malt, oat, rice, rye, and wheat.

"Pulses, seeds, kernels, nuts, and their products" include, but are not limited to, almond, cashew, coffee, cola nut, lima bean, millet, peanut, pinto bean, safflower seed, sesame, soybean, sunflower seed, and walnut.

"Vegetables and vegetable products" include, but are not limited to, broccoli, cabbage, carrot, cauliflower, celery, corn, cucumber, eggplant, green pea, green pepper, iceberg lettuce, mushroom, onion, potato, spinach, squash, string bean, sweet potato, and tomato.

"Fruits and fruit products" include, but are not limited to, apple, avocado, banana, blueberry, cantaloupe, grape, grapefruit, lemon, olive, orange, peach, pineapple, and strawberry.

"Sugar, sugar products, chocolate products, and confectionary" include, but are not limited to, chocolate, honey, and cane sugar.

"Spices and herbs" include, but are not limited to, chili powder, cinnamon, garlic, mustard seed, parsley, tea, and yeast.

"Cross-reactive tissue antigens" include, but are not limited to, lectins, lectins receptors, tropomyosin, smooth muscle, epitheleal cell antigens, enzymes, cytochrome P-450 enzymes, transglutaminases, and others.

Food allergy or food intolerance can result in significant level of antibodies against the dietary antigen. The antibodies are present as saliva IgA or IgM. Saliva can be a source of body fluid for the detection of immune response to dietary antigens present in the nasopharyngeal cavity and gastrointestinal tract and can be obtained with relative ease from a patient. The salivary antibody induction has been widely used as a model system to study secretory responses to ingested material in a patient, primarily because saliva is an easy secretion to collect and analyze.

The detection of antibodies can be performed with an immunoassay. Immunoassays include, but are not limited to, ELISA test, RIA test, latex agglutination, beads assay, and proteomic assays. A preferable immunoassay is the ELISA test. Other immunoassays can be used and the choice of immunoassay can be determined by one of ordinary skill in the art.

A normal reading is derived from a baseline measurement taken from antibody measurements for individuals without symptoms relating to food allergies or food intolerance. A baseline measurement for the test is obtained by observing the antibody measurements for individuals without symptoms relating to food allergies or food intolerance. For example, most readings for antibody measurements from an individual without symptoms relating to food allergies or food intolerance are below a certain reading. Preferably, about 50–100% of the readings from an individual without symptoms relating to food allergies or food intolerance is below the certain reading, more preferably about 60–100%, 70–100%, or 80–100% of the readings, even more preferably about 90–100% of the readings. Hence, preferably, if an individual exhibits antibody measurement two standard deviations above the baseline, the above-normal antibody measurement indicates presence of food allergy or food intolerance.

Additionally, antibodies against cross-reactive tissue antigens may be tested. Cross-reactive tissue antigens include, but are not limited to, lectins, lectins receptors, tropomyosin, smooth muscle, epithelial cell antigens, enzymes, cytochrome P-450 enzymes, and transglutaminase. Ingested dietary antigens may induce antibodies that react with the specific dietary antigen and another antigen, such as a cross-reactive tissue antigen. If antibodies against cross-reactive tissue antigens are tested in addition to the dietary antigens, then the antibodies can be determined to be protective or pathogenic.

About normal levels of antibodies against the dietary antigen and normal levels of antibodies against cross-reactive tissue antigen indicate optimal conditions. Higher than normal levels of antibodies against the dietary antigen and about normal levels of antibodies against cross-reactive tissue antigen indicate food allergy and intolerance without cross-reacting to tissue antigens. About normal levels of antibodies against the dietary antigen and higher than normal levels of antibodies against cross-reactive tissue antigen indicate an autoimmune reaction not related to the dietary antigens. Higher than normal levels of antibodies against the dietary antigen and higher than normal levels of antibodies against cross-reactive tissue antigen indicate a presence of food allergy and intolerance resulting in an autoimmune reaction.

Although other materials and methods similar or equivalent to those described herein can be used in the practice or testing of the preferred embodiments, the preferred method and materials are now described. Example 1 describes the steps in a test for dietary antigens.

EXAMPLE 1

Analytical Methods for Identification and Characterization of Food Allergens

The isolation of proteins and glycoproteins in a native form is the prerequisite for the extraction from foodstuffs. A suitable method for food is the low temperature extraction developed by Clements (24). The foodstuffs are homogenized with cold acetone at −40° C. to separate the phenolic ingredients, which can cause a loss of allergenic activity by enzymatic reactions. The precipitated proteins are washed, lyophilized, and extracted with phosphate buffered saline. The contents of the protein extracts are measured by the method of Bradford (25).

The separation of the different proteins from food is carried out by applying chromatographic and electrophoretic methods. The electrophoretic methods include sodium dodecylsulfate polyacrylamide gel electrophoresis (SDS-PAGE) and isoelectric focusing (IEF). In the case of SDS-PAGE, the separation of the proteins is carried out according to their molecular weight. On the other hand, IEF is used to separate proteins and peptides by their isoelectric points. The electrophoretically-separated proteins in polyacrylamide gels are visualized by silver staining or Coomassie brilliant blue staining (26–27).

Apart from electrophoretic techniques, immunological methods are used with regard to the identification and characterization of allergens (28–38). The specific determination of food allergens can be carried out by immunoblotting and enzyme linked immunosorbent assays (ELISA).

Table 2 shows a diagram of a representative procedure to preparation of dietary antigens and peptides thereof.

TABLE 2

SUMMARY OF ANALYTICAL METHODS FOR PREPARATION OF DIETARY ANTIGENS AND PEPTIDES THEREOF

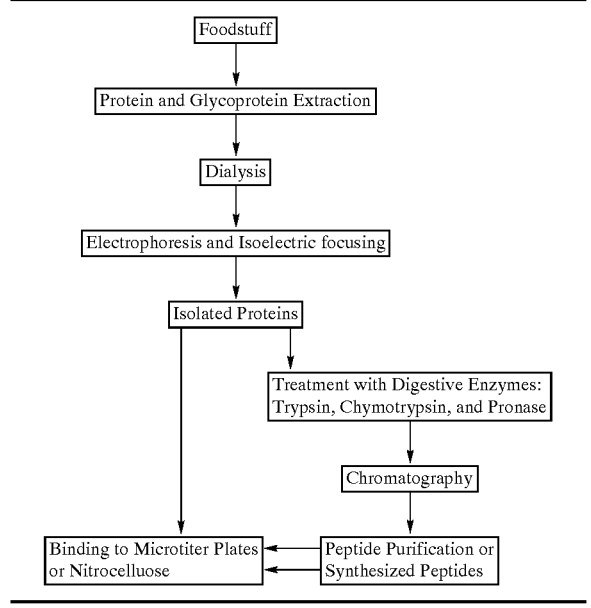

TABLE 2-continued

SUMMARY OF ANALYTICAL METHODS FOR PREPARATION OF DIETARY ANTIGENS AND PEPTIDES THEREOF

· ELISA/RAST
· Immunoblotting

EXAMPLE 2

Test for Dietary Antigens

The immunoassay can use patient saliva, collected in a sterile tube. Saliva can be stored frozen for up to six months at a laboratory, such as Immunosciences Laboratory, in order to be available for testing with samples as necessary to observe the usefulness of treatment.

The purified antigens were prepared according to Example 1 and were immobilized by attachment to a solid surface, such as a microtiter plate. Defined above, the dietary antigens are derived from the following general groups: milk and milk products; eggs and egg products; meat and meat products; fish, mollusks, and crustaceans and their products; oils, fats, and their products; grains and grain products; pulses, seeds, kernels, nuts, and their products; vegetables and vegetable products; fruits and fruit products; sugar, sugar products, chocolate products, and confectionary; and spices and herbs. Test tubes or microtiter plate wells were coated with about 1–10 micrograms of antigens in carbonate buffer about pH 9.5.

The reagents contain sodium azide as a preservative. Sodium azide can react with lead, copper or brass to form explosive metal azides. To prevent the possible formation of explosive metal azides, all the reagents were disposed of by flushing with large amounts of water through the plumbing system. Buffers and other kit components were stored at 2–8° C. before and after dilution.

Saliva samples were collected using sterile tubes. Saliva samples were collected in the morning, before brushing teeth, smoking, or drinking. About 5 ml of saliva was collected. Saliva was collected after a gentle chewing action in a test tube containing about 0.1 ml of preservative. Stored saliva was frozen at −20° C. or lower in tightly sealed sterile tubes. Samples were not repeatedly frozen and thawed and were not stored in self-defrosting freezers because the sample would desiccate and/or immunoglobulin degradation would occur.

The wash buffer was made as follows: in a 500 ml graduated cylinder, 450 ml of water was added to 50 ml of 10× wash buffer. The solution was mixed and transferred to a 500 ml squeeze bottle and stored at 2–8° C. until used. Then, 20 ml of conjugate diluent was added to the anti human IgA or IgM conjugate and mixed well.

Substrate buffer and Stop Solution were ready for use. (CAUTION: Both solutions are caustic: avoid contact with skin and eyes; rinse with copious amounts of water, in the event of contact.)

The substrate solution was prepared only immediately before use. For 1–5 strips, 5 ml of substrate buffer were pipeted into the empty substrate reconstitution bottle and 1 substrate tablet was dropped in. The bottle was shaken to dissolve the tablet. The buffer was used within an hour after reconstitution as recommended.

Reagent and saliva were prepared as follows. All strips to be used, reagents, controls, and patient's saliva were equilibrated to room temperature (22–25° C.). Patient's saliva was diluted 1:5 with saliva diluent buffer, 2 ml saliva+8 ml buffer. Saliva dilutions were made in tubes prior to addition to wells and thoroughly mixed before dispensing. Only one well per test was necessary. Preferably, for every determination, at least 2 strips of eight wells were used to run blank calibrators and patient's samples.

Well Identification: The antigen-coated strips were used. Each was divided into 8 equal-sized squares. As shown in Table 3, in one strip, the top square was labeled "BLANK", the next 6 squares were "CALIBRATOR 1, CALIBRATOR 2, CALIBRATOR 3, CALIBRATOR 4, CALIBRATOR 5, and CALIBRATOR 6". The last one square was labeled anti-food IgA or IgM positive control. Also shown in Table 3, the other strips were coated with the appropriate dietary antigen. In this example, 22 strips of eight wells were used to run about calibrators and patient's samples for about 88 antigens. The tested antigens include American cheese, cheddar cheese, cottage cheese, cow's milk, goat's milk, Swiss cheese, yogurt, eggs, beef, chicken, pork, turkey, clam, codfish, crab, halibut, lobster, oyster, salmon, sardine, scallop, shrimp, sole, trout, tuna, butter, barley, buckwheat, malt, oat, rice, rye, wheat, almond, cashew, coffee, cola nut, lima bean, millet, peanut, pinto bean, safflower seed, sesame, soybean, sunflower seed, walnut, broccoli, cabbage, carrot, cauliflower, celery, corn, cucumber, eggplant, green pea, green pepper, iceberg lettuce, mushroom, onion, potato, spinach, squash, string bean, sweet potato, tomato, apple, avocado, banana, blueberry, cantaloupe, grape, grapefruit, lemon, olive, orange, peach, pineapple, strawberry, chocolate, honey, chili powder, cinnamon, garlic, mustard seed, parsley, tea, Baker's yeast, and Brewer's yeast.

TABLE 3

| Strip 1 | |
|---|---|
| $A_1$ | Blank |
| $B_1$ | Calibrator-1 0.0 u/ml Food IgA or IgM |
| $C_1$ | Calibrator-2 10 u/ml Food IgA or IgM |
| $D_1$ | Calibrator-3 20 u/ml Food IgA or IgM |
| $E_1$ | Calibrator-4 30 u/ml Food IgA or IgM |
| $F_1$ | Calibrator-5 40 u/ml Food IgA or IgM |
| $G_1$ | Calibrator-6 50 u/ml Food IgA or IgM |
| $H_1$ | Anti-food IgA or IgM positive control |

| Strip 2 | Strip 3 | Strip 4 |
|---|---|---|
| $A_2$ Almond | $A_3$ Banana | $A_4$ Broccoli |
| $B_2$ Almond | $B_3$ Banana | $B_4$ Broccoli |
| $C_2$ American Cheese | $C_3$ Barley | $C_4$ Buckwheat |
| $D_2$ American Cheese | $D_3$ Barley | $D_4$ Buckwheat |
| $E_2$ Apple | $E_3$ Beef | $E_4$ Butter |
| $F_2$ Apple | $F_3$ Beef | $F_4$ Butter |
| $G_2$ Avocado | $G_3$ Blueberry | $G_4$ Cabbage |
| $H_2$ Avocado | $H_3$ Blueberry | $H_4$ Cabbage |

| Strip 5 | Strip 6 | Strip 22 |
|---|---|---|
| $A_5$ Cane Sugar | $A_6$ Cauliflower | $A_{22}$ Wheat |
| $B_5$ Cane Sugar | $B_6$ Cauliflower | $B_{22}$ Wheat |
| $C_5$ Cantaloupe | $C_6$ Celery | $C_{22}$ Baker's Yeast |
| $D_5$ Cantaloupe | $D_6$ Celery | $D_{22}$ Baker's Yeast |
| $E_5$ Carrot | $E_6$ Cheddar Cheese | $E_{22}$ Brewer's Yeast |
| $F_2$ Carrot | $F_6$ Cheddar Cheese | $F_{22}$ Brewer's Yeast |
| $G_5$ Cashew | $G_6$ Chicken | $G_{22}$ Yogurt |
| $H_5$ Cashew | $H_6$ Chicken | $H_{22}$ Yogurt |

The assay procedure was as follows: 100 µl of specimen diluent buffer was pipetted into all eight wells of strip #1–22. The contents were discarded. Then, 100 µl of each calibrator or patient specimen dilutions were pipetted into identified wells, patient's samples are run in duplicate wells. Then, 100 µl of specimen diluent buffer was pipetted into a blank well. The reagents were dispensed slowly to avoid splashing and air bubbles. If large air bubbles occurred, they were aspirated or the plate was gently shaken. The plate was covered and incubated for 60 minutes at room temperature (about 22–25° C.). Specimen was shaken from the wells into a container containing disinfectant solution or aspirated with a vacuum device. All wells were emptied prior to filling with 1× wash buffer and allowing a 10–20 second soak time. The wells were emptied by shaking into a disposal container or aspirated. Washing was repeated three more times. The inverted plate was tapped onto a paper towel to completely remove all residual liquid. Then, 100 µl of anti IgA secretory component or anti-IgM conjugate, depending on tested antibody in saliva, was added to the tested strips. The plate was covered and incubated for 60 minutes at room temperature (22–25° C.). The liquid was shaken or aspirated from all the wells and washed four times. Then, 100 µl of p-NPP substrate was added to all wells at timed intervals that corresponded to the reading time of the instrument used to read the reactions. The 45–60-minute incubation time was started as substrate was added to the first well. The plate was covered and incubated 45–60 minutes at 22–25° C. (The assay may be incubated for less than 45 minutes if incubation temperature is higher than 25° C.). Then, 50 µl of 3N NaOH was pipetted into all the wells at the same timed intervals that the p-NPP was added. The plate was shaken for 1–2 minutes by hand or shaker, avoiding splashing. The bottom of the wells was wiped with a non-abrasive paper towel and the instrument was zeroed on the blank well. The O.D. was read at 405±5 nm within 30 minutes and reactions recorded.

The units of IgA or IgM antibody against specific food were determined by a computer program and the use of the following formula:

$$\text{Units/ml of } IgA \text{ or } IgM \text{ Antibody in Saliva (Concentration values)} = \frac{\text{Values of calibrator} \times \text{Absorbance of test specimen}}{\text{Absorbance of calibrator}*}$$

For precise determination, absorbances were converted to concentration values using a point-to-point data reduction method. (However, one may substitute a best-fit linear regression program to obtain values). If a program is used to provide calculation of concentration values, the calibrator concentration values (which appear on vial label) should be entered as the "standards".

The values were obtained manually and plotted using linear graph paper. The X-axis was each calibrator's concentration value. The Y-axis was the corresponding mean absorbance value. A best-fit line was drawn. The concentration value of each patient's saliva was obtained by locating its absorbance on the Y-axis and finding the corresponding concentration value on the X-axis.

EXAMPLE 3

Analysis of Results

Results were analyzed as a panel. The dietary antigens were selected from American cheese, cheddar cheese, cottage cheese, cow's milk, goat's milk, Swiss cheese, yogurt, eggs, beef, chicken, pork, turkey, clam, codfish, crab, halibut, lobster, oyster, salmon, sardine, scallop, shrimp, sole, trout, tuna, butter, barley, buckwheat, malt, oat, rice, rye, wheat, almond, cashew, coffee, cola nut, lima bean, millet, peanut, pinto bean, safflower seed, sesame, soybean, sunflower seed, walnut, broccoli, cabbage, carrot, cauliflower, celery, corn, cucumber, eggplant, green pea, green pepper, iceberg lettuce, mushroom, onion, potato, spinach, squash, string bean, sweet potato, tomato, apple, avocado, banana, blueberry, cantaloupe, grape, grapefruit, lemon, olive, orange, peach, pineapple, strawberry, chocolate, honey, chili powder, cinnamon, garlic, mustard seed, parsley, tea, Baker's yeast, and Brewer's yeast.

Calibration graphs were obtained from the optical density values resulting from the calibration samples for each run. FIGS. 1–6 show calibration graphs of optical density for binding reactions versus concentration of food IgA. FIGS. 7–12 show calibration graphs of optical density for binding reactions versus concentration of food IgM. The calibration graphs can be used to extrapolate concentration values from optical density values obtained from the testing discussed in Example 2. The concentration values of IgA or IgM are compiled for the set of tested dietary antigens for each healthy control and patient. Tables 16–21 show compilation of optical density and concentration values for 88 dietary antigens.

The calibration graphs are obtained from the following calibration readings. The calibration graph shown in FIG. 1 is obtained from Table 4.

TABLE 4

| Sample ID | OD | Concentration (U/ml) | Predicted Concentration (U/ml) |
|---|---|---|---|
| S1 | 0.179 | 0.0 | 4.8 |
| S1 | 0.438 | 10.0 | 10.4 |
| S1 | 0.656 | 20.0 | 15.1 |
| S4 | 1.047 | 30.0 | 23.6 |
| S5 | 1.900 | 40.0 | 42.1 |
| S6 | 2.451 | 50.0 | 54.0 |

Figure 2:
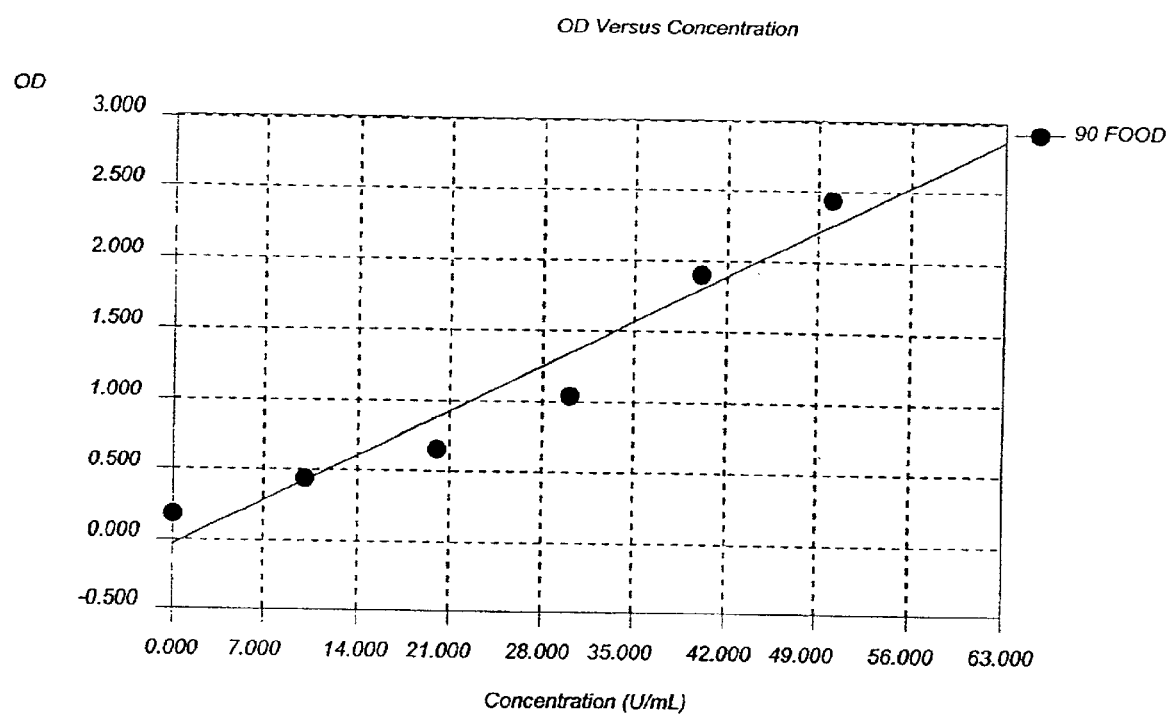

The calibration graph shown in FIG. 2 is obtained from Table 5.

TABLE 5

| Sample ID | OD | Concentration (U/ml) | Predicted Concentration (U/ml) |
|---|---|---|---|
| S1 | 0.180 | 0.0 | 4.7 |
| S1 | 0.442 | 10.0 | 10.4 |
| S1 | 0.657 | 20.0 | 15.1 |
| S4 | 1.047 | 30.0 | 23.6 |
| S5 | 1.905 | 40.0 | 42.2 |
| S6 | 2.447 | 50.0 | 54.0 |

Figure 3:
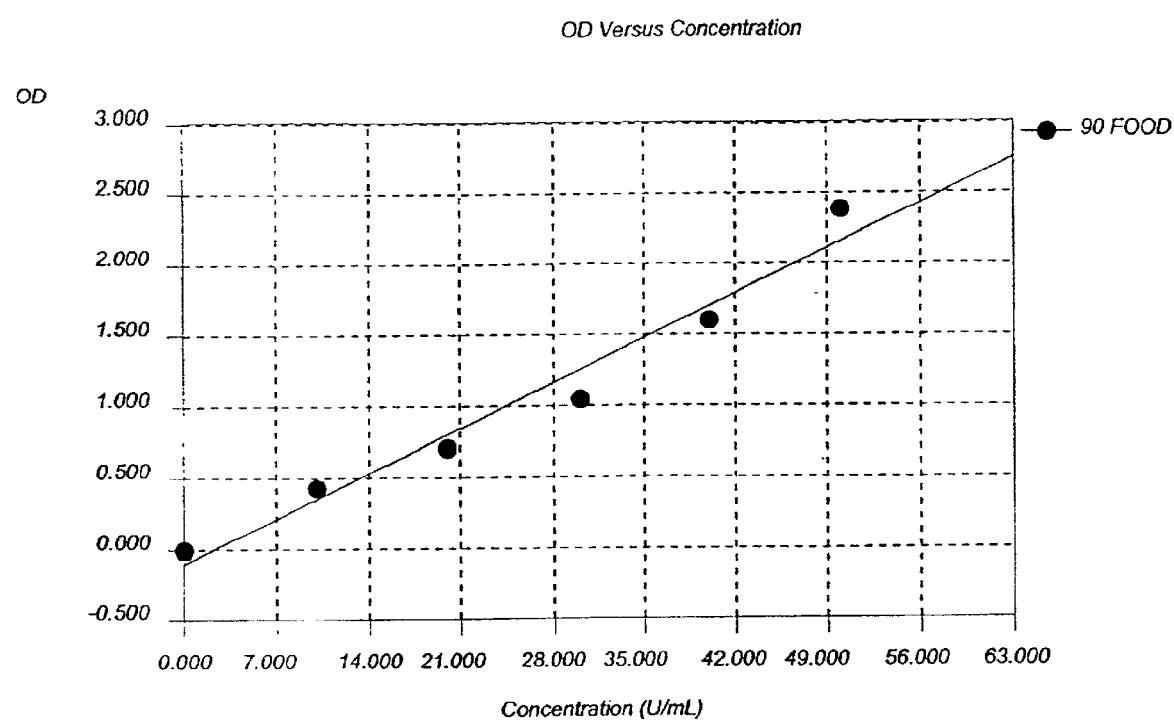

The calibration graph shown in FIG. 3 is obtained from Table 6.

TABLE 6

| Sample ID | OD | Concentration (U/ml) | Predicted Concentration (U/ml) |
|---|---|---|---|
| S1 | −0.006 | 0.0 | 2.2 |
| S1 | 0.423 | 10.0 | 11.7 |
| S1 | 0.709 | 20.0 | 18.0 |
| S4 | 1.041 | 30.0 | 25.3 |
| S5 | 1.604 | 40.0 | 37.7 |
| S6 | 2.389 | 50.0 | 55.1 |

Figure 4:
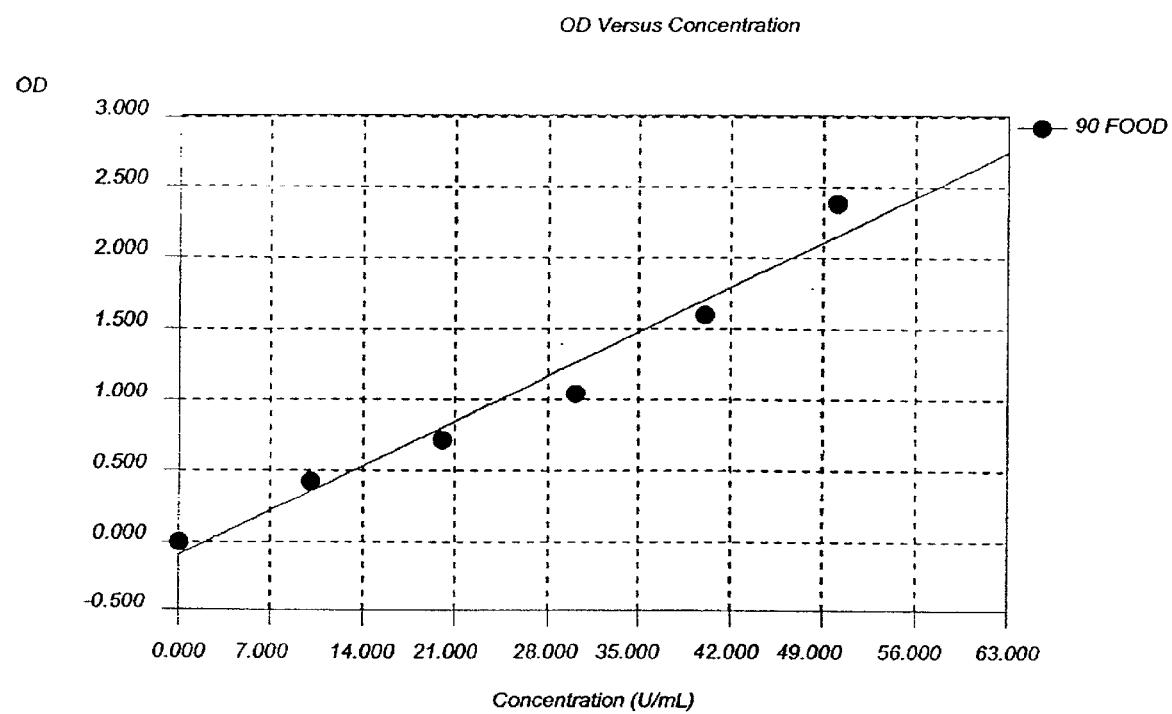

The calibration graph shown in FIG. 4 is obtained from Table 7.

TABLE 7

| Sample ID | OD | Concentration (U/ml) | Predicted Concentration (U/ml) |
|---|---|---|---|
| S1 | −0.005 | 0.0 | 2.1 |
| S1 | 0.425 | 10.0 | 11.6 |
| S1 | 0.723 | 20.0 | 18.2 |
| S4 | 1.044 | 30.0 | 25.3 |
| S5 | 1.606 | 40.0 | 37.8 |
| S6 | 2.384 | 50.0 | 55.0 |

Figure 5:
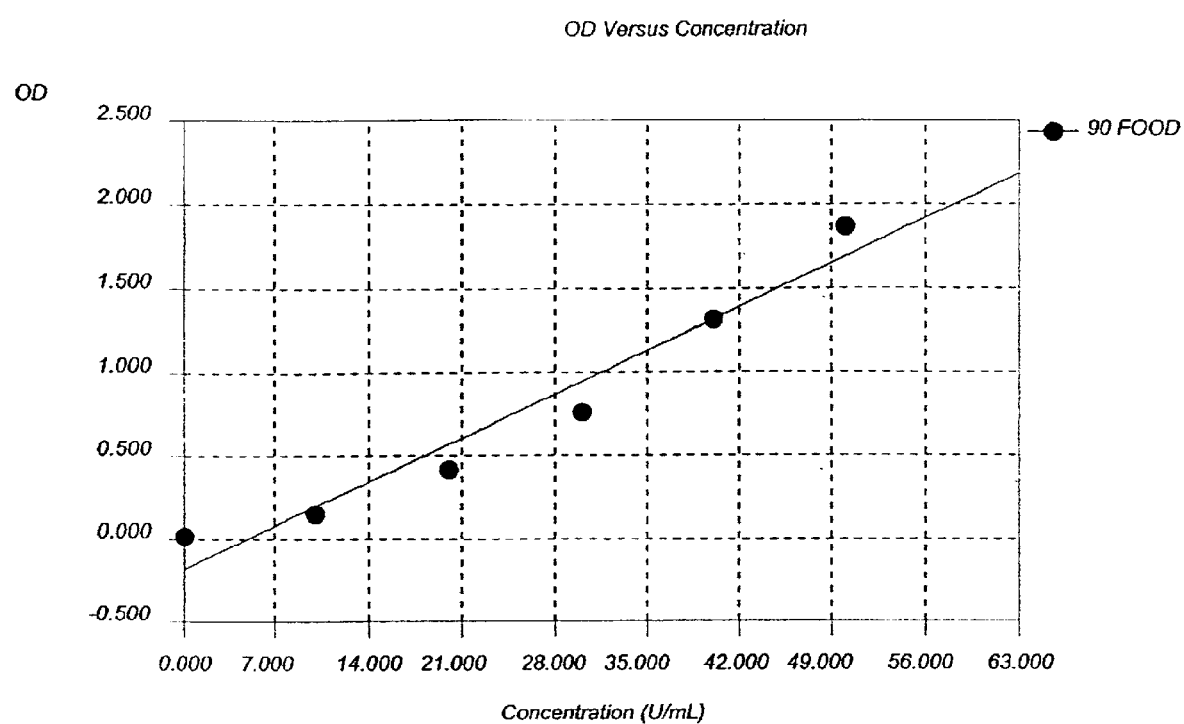

The calibration graph shown in FIG. 5 is obtained from Table 8.

TABLE 8

| Sample ID | OD | Concentration (U/ml) | Predicted Concentration (U/ml) |
|---|---|---|---|
| S1 | 0.026 | 0.0 | 5.4 |
| S1 | 0.153 | 10.0 | 8.8 |
| S1 | 0.421 | 20.0 | 15.9 |
| S4 | 0.763 | 30.0 | 25.0 |
| S5 | 1.329 | 40.0 | 40.1 |
| S6 | 1.878 | 50.0 | 54.8 |

Figure 6:
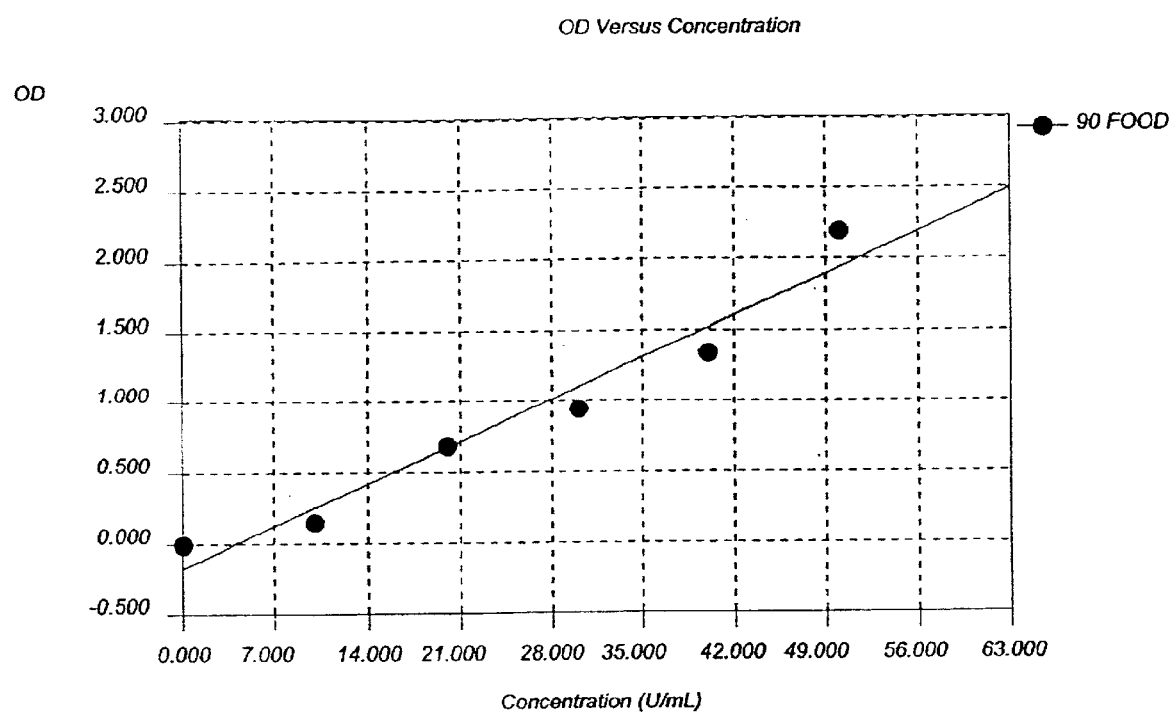

The calibration graph shown in FIG. 6 is obtained from Table 9.

TABLE 9

| Sample ID | OD | Concentration (U/ml) | Predicted Concentration (U/ml) |
|---|---|---|---|
| S1 | −0.002 | 0.0 | 4.1 |
| S1 | 0.148 | 10.0 | 7.6 |
| S1 | 0.683 | 20.0 | 20.2 |
| S4 | 0.946 | 30.0 | 26.4 |
| S5 | 1.335 | 40.0 | 35.6 |
| S6 | 2.199 | 50.0 | 56.0 |

Figure 7:
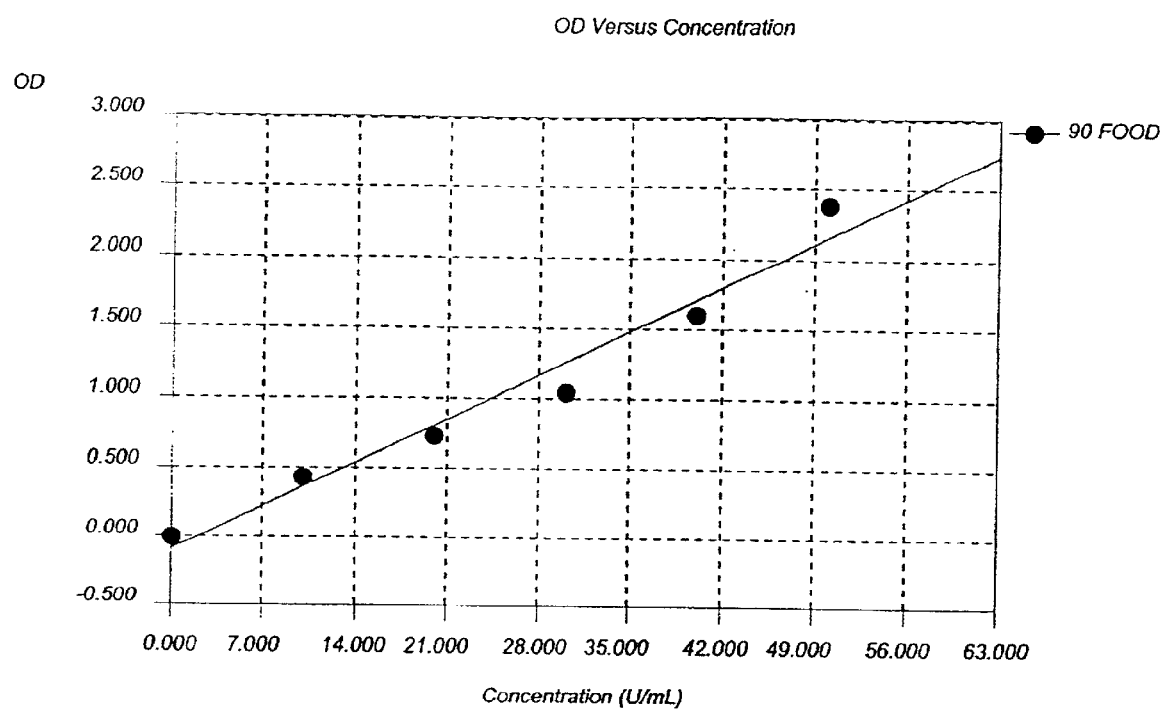
FIGS. 7–12 show calibration graphs of optical density for binding reactions versus concentration of food IgM.

The calibration graph shown in FIG. 7 is obtained from Table 10.

TABLE 10

| Sample ID | OD | Concentration (U/ml) | Predicted Concentration (U/ml) |
|---|---|---|---|
| S1 | −0.002 | 0.0 | 2.1 |
| S1 | 0.429 | 10.0 | 11.6 |
| S1 | 0.725 | 20.0 | 18.2 |
| S4 | 1.046 | 30.0 | 25.3 |
| S5 | 1.605 | 40.0 | 37.7 |
| S6 | 2.338 | 50.0 | 55.0 |

Figure 8:
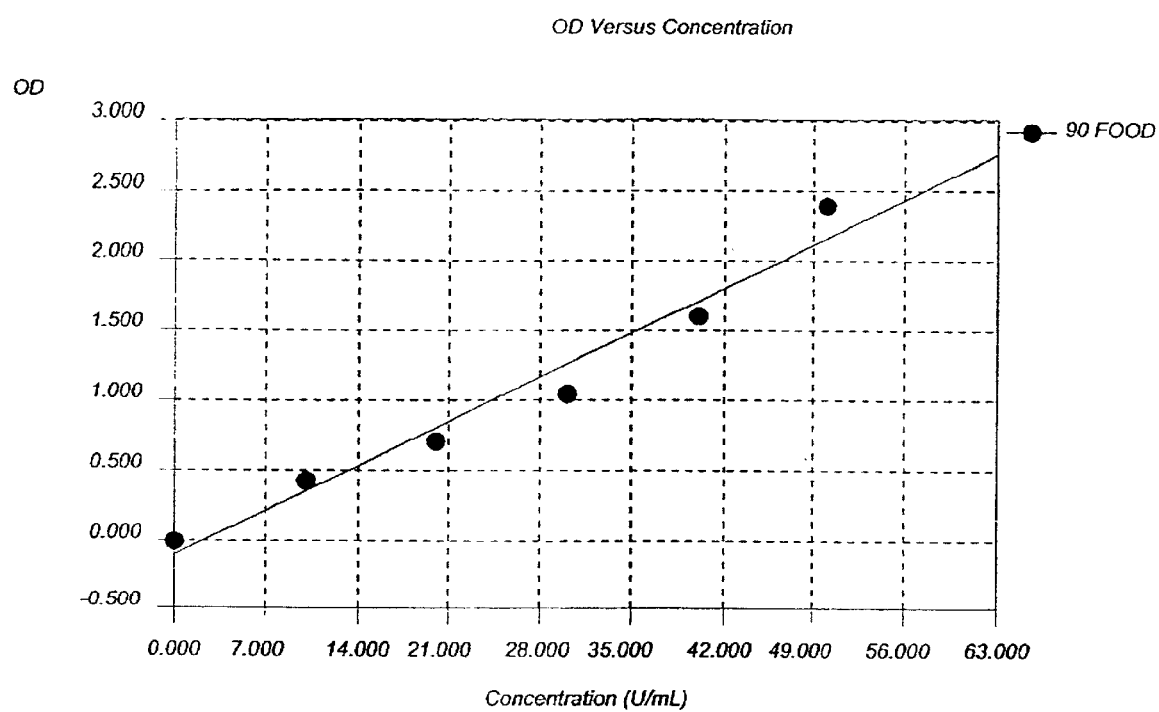

The calibration graph shown in FIG. 8 is obtained from Table 11.

TABLE 11

| Sample ID | OD | Concentration (U/ml) | Predicted Concentration (U/ml) |
|---|---|---|---|
| S1 | −0.004 | 0.0 | 2.2 |
| S1 | 0.426 | 10.0 | 11.7 |
| S1 | 0.710 | 20.0 | 17.9 |
| S4 | 1.044 | 30.0 | 25.3 |
| S5 | 1.607 | 40.0 | 37.7 |
| S6 | 2.402 | 50.0 | 55.2 |

Figure 9:
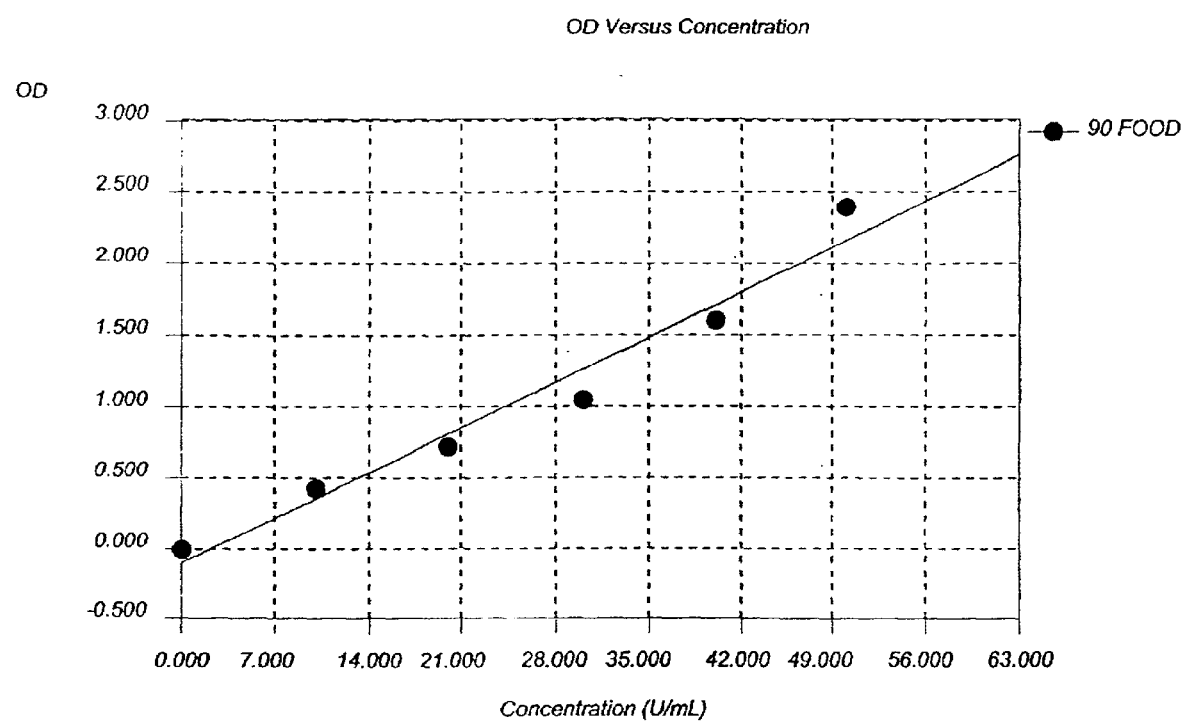

The calibration graph shown in FIG. 9 is obtained from Table 12.

TABLE 12

| Sample ID | OD | Concentration (U/ml) | Predicted Concentration (U/ml) |
|---|---|---|---|
| S1 | −0.003 | 0.0 | 2.2 |
| S1 | 0.427 | 10.0 | 11.7 |
| S1 | 0.716 | 20.0 | 18.0 |
| S4 | 1.044 | 30.0 | 25.3 |
| S5 | 1.611 | 40.0 | 37.8 |
| S6 | 2.397 | 50.0 | 55.1 |

Figure 10:
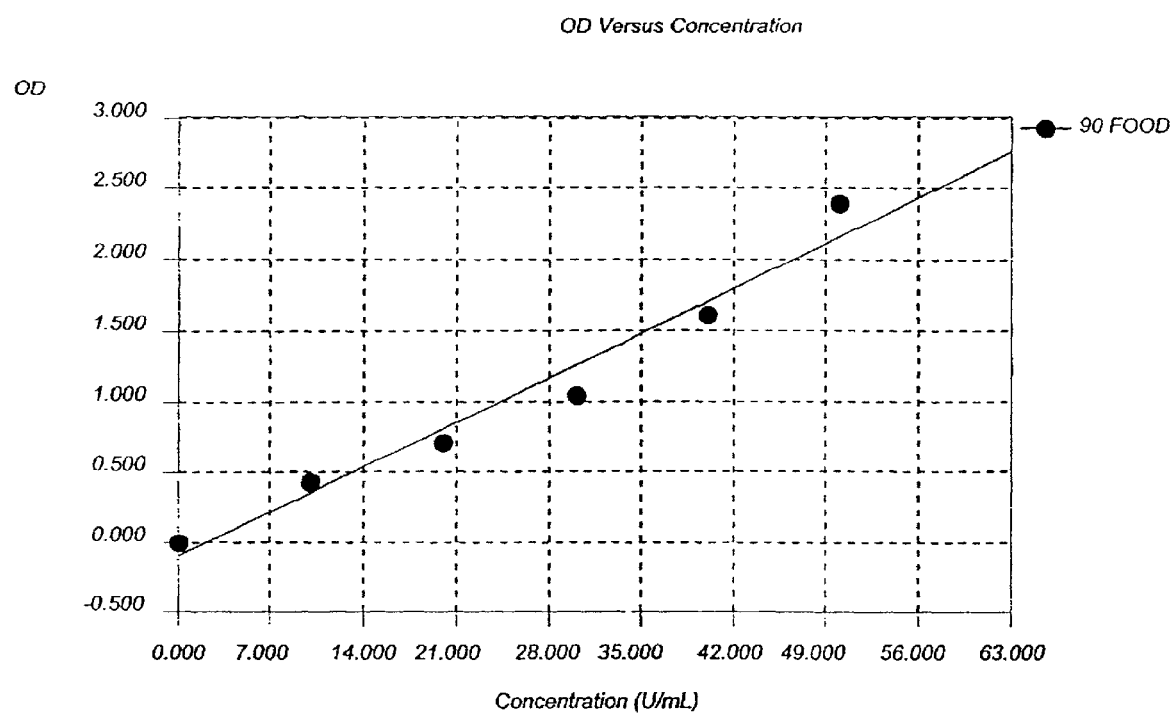

The calibration graph shown in FIG. 10 is obtained from Table 13.

TABLE 13

| Sample ID | OD | Concentration (U/ml) | Predicted Concentration (U/ml) |
|---|---|---|---|
| S1 | −0.001 | 0.0 | 2.2 |
| S1 | 0.431 | 10.0 | 11.7 |
| S1 | 0.709 | 20.0 | 17.9 |
| S4 | 1.048 | 30.0 | 25.3 |
| S5 | 1.613 | 40.0 | 37.8 |
| S6 | 2.395 | 50.0 | 55.1 |

Figure 11:
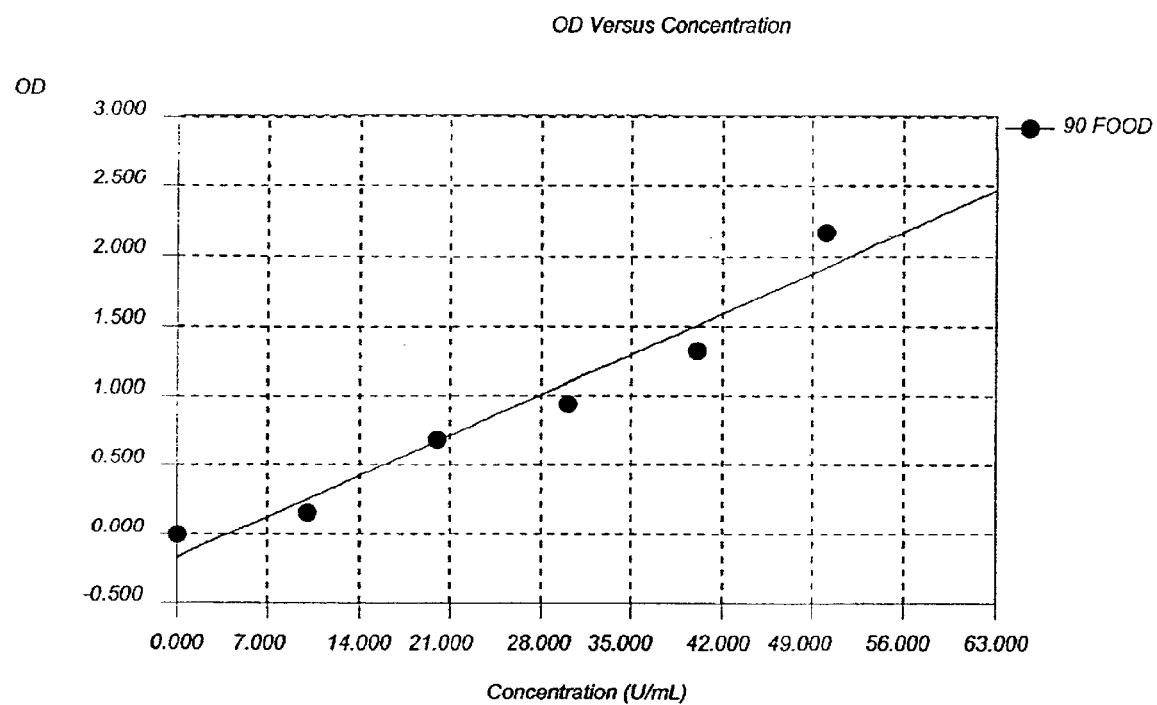

The calibration graph shown in FIG. 11 is obtained from Table 14.

TABLE 14

| Sample ID | OD | Concentration (U/ml) | Predicted Concentration (U/ml) |
|---|---|---|---|
| S1 | −0.001 | 0.0 | 4.0 |
| S1 | 0.155 | 10.0 | 7.7 |
| S1 | 0.678 | 20.0 | 20.2 |
| S4 | 0.941 | 30.0 | 26.5 |
| S5 | 1.328 | 40.0 | 35.7 |
| S6 | 2.174 | 50.0 | 55.9 |

Figure 12:
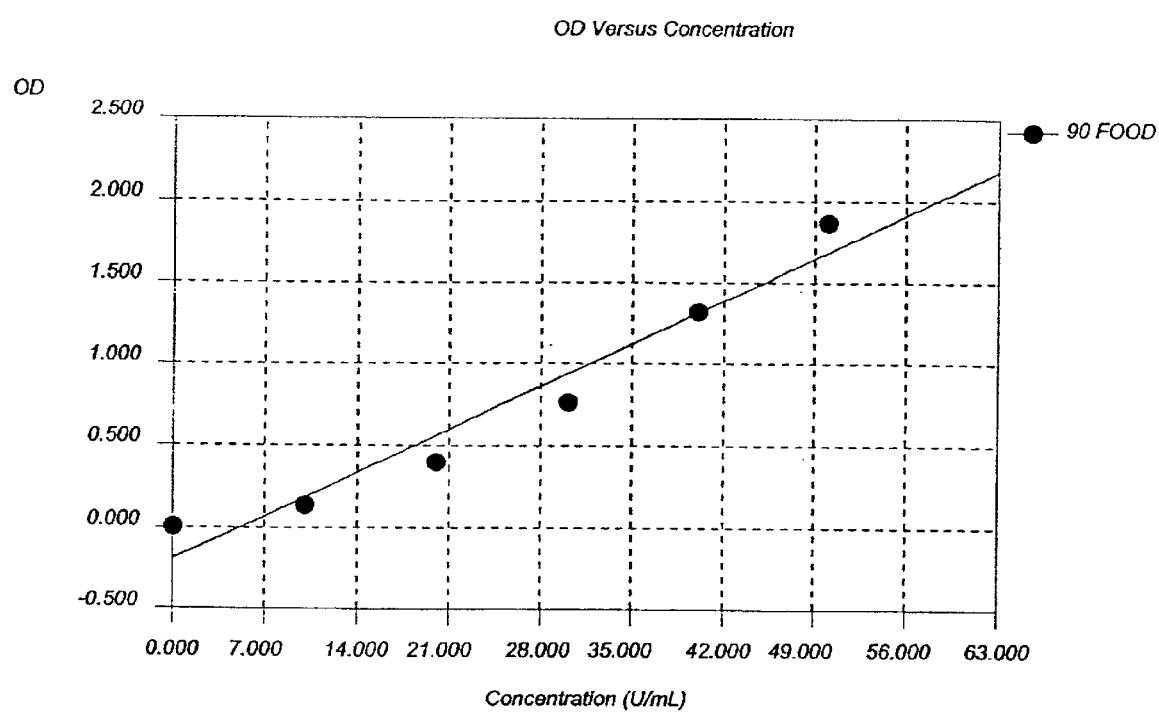

The calibration graph shown in FIG. 12 is obtained from Table 15.

TABLE 15

| Sample ID | OD | Concentration (U/ml) | Predicted Concentration (U/ml) |
|---|---|---|---|
| S1 | 0.014 | 0.0 | 5.4 |
| S1 | 0.147 | 10.0 | 8.9 |
| S1 | 0.402 | 20.0 | 15.7 |
| S4 | 0.761 | 30.0 | 25.2 |
| S5 | 1.322 | 40.0 | 40.1 |
| S6 | 1.870 | 50.0 | 54.7 |

Table 16 shows a compilation of optical density and concentration values for 88 dietary antigens in a healthy control. The antibodies that were tested were IgA. The location specifies the location of the antigen on the test strip. For the data shown in Table 16, two sets of 12 strips were used; each set had its own calibration strip to generate a calibration graph. Each antigen is tested in two wells and the data are averaged from the readings from the two wells. The concentration readings were extrapolated from the average optical density readings and a calibration curve, as shown in FIGS. 1 and 2. FIG. 1 is used to extrapolate data from almond to lima bean in Table 16; FIG. 2 is used to extrapolate data from lobster to yogurt in Table 16. Data from Table 16 indicates that a certain healthy control shows salivary IgA antibody levels against banana and beef at above about 10 U/ml.

TABLE 16

Optical Density and Concentration of Food Specific IgA in Healthy Control

| Sample | Location | OD (data) | OD (mean) | Concentration (U/ml) |
|---|---|---|---|---|
| Almond | A2; B2 | 0.002; 0.001 | 0.002 | 0.9 |
| American cheese | C2; D2 | 0.002; 0.002 | 0.002 | 0.9 |
| Apple | E2; F2 | 0.000; 0.003 | 0.001 | 0.9 |
| Avocado | G2; H2 | 0.005; 0.002 | 0.003 | 1.0 |
| Banana | A3; B3 | 0.484; 0.407 | 0.445 | 10.5 |
| Barley | C3; D3 | 0.200; 0.216 | 0.208 | 5.4 |
| Beef | E3; F3 | 0.500; 0.405 | 0.452 | 10.7 |
| Blueberry | G3; H3 | 0.001; 0.003 | 0.002 | 0.9 |
| Broccoli | A4; B4 | 0.001; 0.000 | 0.000 | 0.9 |
| Buckwheat | C4; D4 | 0.002; 0.001 | 0.001 | 0.9 |
| Butter | E4; F4 | 0.001; 0.001 | 0.001 | 0.9 |
| Cabbage | G4; H4 | 0.003; 0.003 | 0.003 | 0.9 |
| Cantaloupe | A5; B5 | 0.102; 0.075 | 0.089 | 2.8 |
| Carrot | C5; D5 | 0.005; 0.005 | 0.005 | 1.0 |
| Cashew | E5; F5 | 0.181; 0.162 | 0.171 | 4.6 |
| Cauliflower | G5; H5 | 0.003; 0.017 | 0.010 | 1.1 |
| Celery | A6; B6 | 0.000; 0.000 | 0.000 | 0.9 |
| Cheddar cheese | C6; D6 | 0.001; 0.006 | 0.003 | 0.9 |
| Chicken | E6; F6 | 0.005; 0.005 | 0.005 | 1.0 |
| Chili powder | G6; H6 | 0.136; 0.106 | 0.121 | 3.5 |
| Chocolate | A7; B7 | 0.008; 0.007 | 0.008 | 1.0 |
| Cinnamon | C7; D7 | 0.001; 0.001 | 0.001 | 0.9 |
| Clam | E7; F7 | 0.142; 0.338 | 0.240 | 6.1 |
| Codfish | G7; H7 | 0.002; 0.003 | 0.002 | 0.9 |
| Coffee | A8; B8 | 0.005; 0.009 | 0.007 | 1.0 |
| Cola nut | C8; D8 | 0.008; 0.006 | 0.007 | 1.0 |
| Corn | E8; F8 | 0.015; 0.012 | 0.013 | 1.2 |
| Cottage cheese | G8; H8 | 0.228; 0.170 | 0.199 | 5.2 |
| Cow's milk | A9; B9 | 0.001; 0.002 | 0.001 | 0.9 |
| Crab | C9; D9 | 0.014; 0.206 | 0.110 | 3.3 |
| Cucumber | E9; F9 | 0.002; 0.001 | 0.002 | 0.9 |
| Egg | G9; H9 | 0.003; 0.002 | 0.002 | 0.9 |
| Eggplant | A10; B10 | 0.015; 0.005 | 0.010 | 1.1 |
| Garlic | C10; D10 | 0.038; 0.010 | 0.024 | 1.4 |
| Goat's milk | E10; F10 | 0.241; 0.211 | 0.226 | 5.8 |
| Grape | G10; H10 | 0.016; 0.028 | 0.022 | 1.4 |
| Grapefruit | A11; B11 | 0.225; 0.275 | 0.250 | 6.3 |
| Green pea | C11; D11 | 0.001; 0.007 | 0.004 | 1.0 |
| Green pepper | E11; F11 | 0.087; 0.002 | 0.044 | 1.8 |
| Halibut | G11; H11 | 0.010; 0.034 | 0.022 | 1.4 |
| Honey | A12; B12 | 0.005; 0.002 | 0.003 | 1.0 |
| Lettuce, iceberg | C12; D12 | −0.001; 0.310 | 0.154 | 4.2 |
| Lemon | E12; F12 | 0.335; 0.003 | 0.169 | 4.5 |
| Lima bean | G12; H12 | 0.238; 0.235 | 0.237 | 6.0 |
| Lobster | A2; B2 | −0.002; 0.001 | 0.001 | 0.8 |
| Malt | C2; D2 | 0.160; 0.010 | 0.085 | 2.7 |
| Millet | E2; F2 | 0.001; 0.003 | 0.002 | 0.9 |
| Mushroom | G2; H2 | 0.003; 0.005 | 0.004 | 0.9 |
| Mustard seed | A3; B3 | 0.002; 0.000 | 0.001 | 0.8 |
| Oat | C3; D3 | 0.001; 0.105 | 0.053 | 2.0 |
| Olive | E3; F3 | 0.003; 0.003 | 0.003 | 0.9 |
| Onion | G3; H3 | 0.000; 0.006 | 0.003 | 0.9 |
| Orange | A4; B4 | 0.002; 0.004 | 0.003 | 0.9 |
| Oyster | C4; D4 | 0.363; 0.285 | 0.324 | 7.9 |
| Parsley | E4; F4 | 0.002; 0.003 | 0.002 | 0.9 |
| Peach | G4; H4 | 0.003; 0.001 | 0.002 | 0.9 |
| Peanut | A5; B5 | 0.263; 0.238 | 0.251 | 6.3 |
| Pinto bean | C5; D5 | 0.002; 0.005 | 0.003 | 0.9 |
| Pineapple | E5; F5 | 0.001; 0.001 | 0.001 | 0.8 |
| Pork | G5; H5 | 0.004; 0.001 | 0.002 | 0.9 |
| Potato | A6; B6 | 0.004; 0.002 | 0.003 | 0.9 |
| Rice | C6; D6 | 0.001; 0.003 | 0.002 | 0.9 |
| Rye | E6; F6 | 0.004; 0.007 | 0.006 | 0.9 |
| Safflower seed | G6; H6 | 0.002; 0.006 | 0.004 | 0.9 |
| Salmon | A7; B7 | 0.004; 0.002 | 0.003 | 0.9 |
| Sardine | C7; D7 | 0.002; 0.002 | 0.002 | 0.9 |
| Scallop | E7; F7 | 0.014; 0.002 | 0.008 | 1.0 |
| Sesame | G7; H7 | 0.003; 0.008 | 0.006 | 0.9 |
| Shrimp | A8; B8 | 0.007; 0.008 | 0.008 | 1.0 |
| Sole | C8; D8 | 0.228; 0.247 | 0.238 | 6.0 |
| Soybean | E8; F8 | 0.004; 0.004 | 0.004 | 0.9 |
| Spinach | G8; H8 | 0.239; 0.218 | 0.229 | 5.8 |
| Squash | A9; B9 | −0.002; 0.002 | 0.000 | 0.8 |

TABLE 16-continued

Optical Density and Concentration of
Food Specific IgA in Healthy Control

| Sample | Location | OD (data) | OD (mean) | Concentration (U/ml) |
|---|---|---|---|---|
| Strawberry | C9; D9 | 0.003; 0.006 | 0.005 | 0.9 |
| String bean | E9; F9 | 0.007; 0.003 | 0.005 | 0.9 |
| Sunflower seed | G9; H9 | 0.003; 0.002 | 0.002 | 0.9 |
| Sweet potato | A10; B10 | 0.008; 0.017 | 0.013 | 1.1 |
| Swiss cheese | C10; D10 | 0.082; 0.003 | 0.042 | 1.7 |
| Tea, black | E10; F10 | 0.015; 0.008 | 0.012 | 1.1 |
| Tomato | G10; H10 | 0.008; 0.005 | 0.007 | 1.0 |
| Trout | A11; B11 | 0.000; 0.002 | 0.001 | 0.8 |
| Tuna | C11; D11 | 0.002; 0.002 | 0.002 | 0.9 |
| Turkey | E11; F11 | 0.003; 0.001 | 0.002 | 0.9 |
| Walnut, black | G11; H11 | 0.226; 0.210 | 0.218 | 5.6 |
| Wheat | A12; B12 | 0.002; 0.002 | 0.002 | 0.9 |
| Yeast, Baker's | C12; D12 | 0.342; 0.216 | 0.279 | 6.9 |
| Yeast, Brewer's | E12; F12 | 0.004; 0.001 | 0.003 | 0.9 |
| Yogurt | G12; H12 | 0.003; 0.003 | 0.003 | 0.9 |

Table 17 shows a compilation of optical density and concentration values for 88 dietary antigens in a patient with moderate food allergy and food intolerance. The antibodies that were tested were IgA. The location specifies the location of the antigen on the test strip. For the data shown in Table 17, two sets of 12 strips were used; each set had its own calibration strip to generate a calibration graph. Each antigen is tested in two wells and the data are averaged from the readings from the two wells. The concentration readings were extrapolated from the average optical density readings and a calibration curve, as shown in FIGS. 3 and 4. FIG. 3 is used to extrapolate data from almond to lima bean in Table 17; FIG. 4 is used to extrapolate data from lobster to yogurt in Table 17. Data from Table 17 indicates that a certain patient with moderate food allergy and food intolerance shows salivary IgA antibody levels against banana, cashew, crab, grapefruit, lima bean, malt, peanut, spinach, and Baker's yeast at above about 15 U/ml.

TABLE 17

Optical Density and Concentration of Food Specific IgA in
Patient with Moderate Food Allergy and Food Intolerance

| Sample | Location | OD (data) | OD (mean) | Concentration (U/ml) |
|---|---|---|---|---|
| Almond | A2; B2 | −0.004; −0.005 | −0.005 | 2.2 |
| American cheese | C2; D2 | −0.004; −0.004 | −0.004 | 2.2 |
| Apple | E2; F2 | −0.006; −0.003 | −0.005 | 2.2 |
| Avocado | G2; H2 | −0.002; −0.004 | −0.003 | 2.3 |
| Banana | A3; B3 | 0.991; 0.839 | 0.915 | 22.5 |
| Barley | C3; D3 | −0.005; −0.005 | −0.005 | 2.2 |
| Beef | E3; F3 | 0.545; 0.465 | 0.505 | 13.5 |
| Blueberry | G3; H3 | −0.005; −0.003 | −0.004 | 2.2 |
| Broccoli | A4; B4 | −0.006; −0.006 | −0.006 | 2.2 |
| Buckwheat | C4; D4 | −0.005; −0.005 | −0.005 | 2.2 |
| Butter | E4; F4 | −0.005; −0.005 | −0.005 | 2.2 |
| Cabbage | G4; H4 | −0.004; −0.003 | −0.003 | 2.3 |
| Cantaloupe | A5; B5 | 0.140; 0.111 | 0.125 | 5.1 |
| Carrot | C5; D5 | −0.001; −0.001 | −0.001 | 2.3 |
| Cashew | E5; F5 | 1.544; 1.321 | 1.432 | 34.0 |
| Cauliflower | G5; H5 | −0.003; 0.011 | 0.004 | 2.4 |
| Celery | A6; B6 | −0.006; −0.007 | −0.006 | 2.2 |
| Cheddar cheese | C6; D6 | −0.006; −0.001 | −0.003 | 2.3 |
| Chicken | E6; F6 | −0.001; −0.002 | −0.002 | 2.3 |
| Chili powder | G6; H6 | 0.000; −0.006 | −0.003 | 2.3 |
| Chocolate | A7; B7 | −0.007; −0.005 | −0.006 | 2.2 |
| Cinnamon | C7; D7 | −0.005; −0.005 | −0.005 | 2.2 |
| Clam | E7; F7 | −0.003; −0.004 | −0.003 | 2.2 |
| Codfish | G7; H7 | −0.005; −0.004 | −0.004 | 2.2 |

TABLE 17-continued

Optical Density and Concentration of Food Specific IgA in
Patient with Moderate Food Allergy and Food Intolerance

| Sample | Location | OD (data) | OD (mean) | Concentration (U/ml) |
|---|---|---|---|---|
| Coffee | A8; B8 | −0.002; 0.003 | 0.001 | 2.3 |
| Cola nut | C8; D8 | 0.001; −0.001 | 0.000 | 2.3 |
| Corn | E8; F8 | 0.009; 0.005 | 0.007 | 2.5 |
| Cottage cheese | G8; H8 | 0.434; 0.339 | 0.387 | 10.9 |
| Cow's milk | A9; B9 | −0.005; −0.005 | −0.005 | 2.2 |
| Crab | C9; D9 | 1.333; 1.427 | 1.380 | 32.8 |
| Cucumber | E9; F9 | −0.005; −0.006 | −0.005 | 2.2 |
| Egg | G9; H9 | −0.003; −0.005 | −0.004 | 2.2 |
| Eggplant | A10; B10 | 0.008; −0.003 | 0.003 | 2.4 |
| Garlic | C10; D10 | 0.030; 0.003 | 0.017 | 2.7 |
| Goat's milk | E10; F10 | 0.235; 0.205 | 0.220 | 7.2 |
| Grape | G10; H10 | 0.010; 0.022 | 0.016 | 2.7 |
| Grapefruit | A11; B11 | 1.293; 1.252 | 0.273 | 30.4 |
| Green pea | C11; D11 | −0.005; −0.005 | −0.005 | 2.2 |
| Green pepper | E11; F11 | −0.005; −0.005 | −0.005 | 2.2 |
| Halibut | G11; H11 | 0.003; 0.013 | 0.008 | 2.5 |
| Honey | A12; B12 | −0.001; −0.004 | −0.003 | 2.3 |
| Lettuce, iceberg | C12; D12 | −0.007; −0.005 | −0.006 | 2.2 |
| Lemon | E12; F12 | −0.005; −0.004 | −0.004 | 2.2 |
| Lima bean | G12; H12 | 1.394; 1.171 | 1.283 | 30.7 |
| Lobster | A2; B2 | −0.005; −0.004 | −0.004 | 2.1 |
| Malt | C2; D2 | 1.007; 1.008 | 1.008 | 24.5 |
| Millet | E2; F2 | −0.004; −0.003 | −0.004 | 2.1 |
| Mushroom | G2; H2 | −0.003; −0.002 | −0.003 | 2.2 |
| Mustard seed | A3; B3 | −0.003; −0.004 | −0.004 | 2.1 |
| Oat | C3; D3 | −0.004; −0.004 | −0.004 | 2.1 |
| Olive | E3; F3 | −0.002; −0.002 | −0.002 | 2.2 |
| Onion | G3; H3 | −0.004; 0.002 | −0.001 | 2.2 |
| Orange | A4; B4 | −0.003; −0.001 | −0.002 | 2.2 |
| Oyster | C4; D4 | −0.005; −0.003 | −0.004 | 2.1 |
| Parsley | E4; F4 | −0.004; −0.004 | −0.004 | 2.1 |
| Peach | G4; H4 | −0.004; −0.004 | −0.004 | 2.1 |
| Peanut | A5; B5 | 0.684; 0.768 | 0.726 | 18.3 |
| Pinto bean | C5; D5 | −0.003; 0.000 | −0.002 | 2.2 |
| Pineapple | E5; F5 | −0.004; −0.005 | −0.004 | 2.1 |
| Pork | G5; H5 | −0.002; −0.004 | −0.003 | 2.2 |
| Potato | A6; B6 | −0.002; −0.004 | −0.003 | 2.1 |
| Rice | C6; D6 | −0.004; −0.001 | −0.003 | 2.2 |
| Rye | E6; F6 | 0.001; 0.002 | 0.001 | 2.2 |
| Safflower seed | G6; H6 | −0.003; −0.001 | −0.002 | 2.2 |
| Salmon | A7; B7 | −0.001; −0.003 | −0.002 | 2.2 |
| Sardine | C7; D7 | −0.003; −0.003 | −0.003 | 2.2 |
| Scallop | E7; F7 | 0.429; 0.473 | 0.451 | 12.2 |
| Sesame | G7; H7 | −0.001; 0.004 | 0.001 | 2.2 |
| Shrimp | A8; B8 | 0.002; 0.015 | 0.009 | 2.4 |
| Sole | C8; D8 | 0.007; −0.001 | 0.003 | 2.3 |
| Soybean | E8; F8 | 0.003; 0.001 | 0.002 | 2.3 |
| Spinach | G8; H8 | 0.812; 0.744 | 0.778 | 19.4 |
| Squash | A9; B9 | −0.003; −0.004 | −0.004 | 2.1 |
| Strawberry | C9; D9 | −0.002; 0.002 | 0.000 | 2.2 |
| String bean | E9; F9 | −0.004; −0.001 | −0.003 | 2.2 |
| Sunflower seed | G9; H9 | −0.003; −0.004 | −0.003 | 2.1 |
| Sweet potato | A10; B10 | 0.003; 0.014 | 0.009 | 2.4 |
| Swiss cheese | C10; D10 | 0.015; 0.003 | 0.009 | 2.4 |
| Tea, black | E10; F10 | 0.017; 0.004 | 0.010 | 2.4 |
| Tomato | G10; H10 | 0.011; 0.000 | 0.006 | 2.3 |
| Trout | A11; B11 | −0.006; −0.003 | −0.005 | 2.1 |
| Tuna | C11; D11 | −0.004; −0.002 | −0.003 | 2.2 |
| Turkey | E11; F11 | −0.001; −0.003 | −0.002 | 2.2 |
| Walnut, black | G11; H11 | −0.003; 0.000 | −0.001 | 2.2 |
| Wheat | A12; B12 | −0.003; −0.004 | −0.004 | 2.1 |
| Yeast, Baker's | C12; D12 | 0.851; 0.684 | 0.767 | 19.2 |
| Yeast, Brewer's | E12; F12 | −0.001; −0.004 | −0.003 | 2.2 |
| Yogurt | G12; H12 | −0.003; −0.003 | −0.003 | 2.1 |

Table 18 shows a compilation of optical density and concentration values for 88 dietary antigens in a patient with severe food allergy and food intolerance. The antibodies that were tested were IgA. The location specifies the location of the antigen on the test strip. For the data shown in Table 18, two sets of 12 strips were used; each set had its own calibration strip to generate a calibration graph. Each antigen is tested in two wells and the data are averaged from the readings from the two wells. The concentration readings were extrapolated from the average optical density readings and a calibration curve, as shown in FIGS. 5 and 6. FIG. 5 is used to extrapolate data from almond to lima bean in Table 18; FIG. 6 is used to extrapolate data from lobster to yogurt in Table 18. Data from Table 18 indicates that a patient with severe food allergy and food intolerance shows salivary IgA antibody levels against apple, banana, blueberry, cantaloupe, cauliflower, cheddar cheese, codfish, cola nut, cow's milk, grapes, grapefruit, lettuce, mushroom, pineapple, safflower seed, shrimp soybean, Swiss cheese, Baker's yeast, and Brewer's yeast at above about 20 U/ml.

TABLE 18

Optical Density and Concentration of Food Specific IgA in Patient with Severe Food Allergy and Food Intolerance

| Sample | Location | OD (data) | OD (mean) | Concentration (U/ml) |
|---|---|---|---|---|
| Almond | A2; B2 | −0.078; −0.079 | −0.079 | 2.6 |
| American cheese | C2; D2 | −0.093; −0.088 | −0.090 | 2.3 |
| Apple | E2; F2 | 1.330; 0.198 | 1.264 | 38.4 |
| Avocado | G2; H2 | −0.076; −0.083 | −0.079 | 2.6 |
| Banana | A3; B3 | 1.416; 1.317 | 1.366 | 41.1 |
| Barley | C3; D3 | −0.077; −0.076 | −0.077 | 2.6 |
| Beef | E3; F3 | −0.077; −0.081 | −0.079 | 2.6 |
| Blueberry | G3; H3 | 0.645; 0.607 | 0.626 | 21.4 |
| Broccoli | A4; B4 | −0.077; −0.069 | −0.073 | 2.8 |
| Buckwheat | C4; D4 | 0.355; 0.363 | 0.359 | 14.3 |
| Butter | E4; F4 | −0.055; −0.079 | −0.067 | 2.9 |
| Cabbage | G4; H4 | −0.064; −0.072 | −0.068 | 2.9 |
| Cantaloupe | A5; B5 | 1.224; 1.153 | 1.188 | 36.4 |
| Carrot | C5; D5 | −0.070; −0.078 | −0.074 | 2.7 |
| Cashew | E5; F5 | −0.073; −0.068 | −0.070 | 2.8 |
| Cauliflower | G5; H5 | 1.072; 1.261 | 1.166 | 35.8 |
| Celery | A6; B6 | −0.073; −0.079 | −0.076 | 2.7 |
| Cheddar cheese | C6; D6 | 1.096; 1.030 | 1.063 | 33.0 |
| Chicken | E6; F6 | −0.075; −0.073 | −0.074 | 2.7 |
| Chili powder | G6; H6 | −0.062; −0.064 | −0.063 | 3.0 |
| Chocolate | A7; B7 | −0.076; −0.071 | −0.073 | 2.7 |
| Cinnamon | C7; D7 | −0.076; −0.075 | −0.075 | 2.7 |
| Clam | E7; F7 | −0.069; 0.079 | −0.074 | 2.7 |
| Codfish | G7; H7 | 0.757; 0.790 | 0.774 | 25.3 |
| Coffee | A8; B8 | −0.078; −0.075 | −0.076 | 2.7 |
| Cola nut | C8; D8 | 0.746; 1.006 | 0.876 | 28.0 |
| Corn | E8; F8 | −0.080; −0.029 | −0.054 | 3.2 |
| Cottage cheese | G8; H8 | −0.069; −0.067 | −0.068 | 2.9 |
| Cow's milk | A9; B9 | 0.682; 0.748 | 0.715 | 23.8 |
| Crab | C9; D9 | −0.074; −0.075 | −0.075 | 2.7 |
| Cucumber | E9; F9 | 0.588; 0.553 | 0.570 | 19.9 |
| Egg | G9; H9 | −0.073; −0.078 | −0.076 | 2.7 |
| Eggplant | A10; B10 | −0.078; −0.079 | −0.079 | 2.6 |
| Garlic | C10; D10 | −0.080; −0.047 | −0.063 | 3.0 |
| Goat's milk | E10; F10 | −0.076; −0.075 | −0.076 | 2.7 |
| Grape | G10; H10 | 0.848; 0.937 | 0.893 | 28.5 |
| Grapefruit | A11; B11 | 0.815; 0.909 | 0.862 | 27.7 |
| Green pea | C11; D11 | −0.079; −0.071 | −0.075 | 2.7 |
| Green pepper | E11; F11 | −0.069; −0.064 | −0.067 | 2.9 |
| Halibut | G11; H11 | 0.534; 0.605 | 0.569 | 19.9 |
| Honey | A12; B12 | −0.079; −0.081 | −0.080 | 2.6 |
| Lettuce, iceberg | C12; D12 | 1.387; 0.831 | 1.109 | 34.3 |
| Lemon | E12; F12 | −0.080; −0.077 | −0.079 | 2.6 |
| Lima bean | G12; H12 | −0.075; −0.076 | −0.075 | 2.7 |
| Lobster | A2; B2 | −0.012; −0.013 | −0.013 | 3.8 |
| Malt | C2; D2 | 0.500; 0.573 | 0.537 | 16.8 |
| Millet | E2; F2 | −0.014; −0.012 | −0.013 | 3.8 |
| Mushroom | G2; H2 | 1.541; 1.500 | 1.520 | 40.0 |
| Mustard seed | A3; B3 | 0.423; 0.354 | 0.388 | 13.3 |
| Oat | C3; D3 | −0.013; −0.015 | −0.014 | 3.8 |
| Olive | E3; F3 | −0.013; −0.011 | −0.012 | 3.8 |
| Onion | G3; H3 | −0.013; −0.012 | −0.013 | 3.8 |
| Orange | A4; B4 | −0.014; −0.014 | −0.014 | 3.8 |
| Oyster | C4; D4 | −0.013; −0.014 | −0.013 | 3.8 |
| Parsley | E4; F4 | 0.550; 0.492 | 0.521 | 16.4 |
| Peach | G4; H4 | −0.012; −0.006 | −0.009 | 3.9 |

TABLE 18-continued

Optical Density and Concentration of Food Specific IgA in Patient with Severe Food Allergy and Food Intolerance

| Sample | Location | OD (data) | OD (mean) | Concentration (U/ml) |
|---|---|---|---|---|
| Peanut | A5; B5 | 0.077; 0.054 | 0.065 | 5.7 |
| Pinto bean | C5; D5 | −0.010; −0.009 | −0.010 | 3.9 |
| Pineapple | E5; F5 | 1.887; 1.993 | 1.910 | 49.2 |
| Pork | G5; H5 | −0.012; 0.000 | −0.006 | 4.0 |
| Potato | A6; B6 | 0.737; 0.760 | 0.748 | 21.8 |
| Rice | C6; D6 | −0.014; −0.008 | −0.011 | 3.9 |
| Rye | E6; F6 | −0.014; −0.009 | −0.012 | 3.8 |
| Safflower seed | G6; H6 | 0.890; 0.973 | 0.932 | 26.1 |
| Salmon | A7; B7 | −0.019; −0.013 | −0.016 | 3.7 |
| Sardine | C7; D7 | −0.014; −0.013 | −0.013 | 3.8 |
| Scallop | E7; F7 | −0.012; −0.009 | −0.011 | 3.9 |
| Sesame | G7; H7 | −0.013; −0.012 | −0.012 | 3.8 |
| Shrimp | A8; B8 | 1.673; 1.774 | 1.723 | 44.8 |
| Sole | C8; D8 | −0.005; −0.012 | −0.009 | 3.9 |
| Soybean | E8; F8 | 1.459; 1.531 | 1.495 | 39.4 |
| Spinach | G8; H8 | 0.205; 0.146 | 0.176 | 8.3 |
| Squash | A9; B9 | −0.014; −0.013 | −0.013 | 3.8 |
| Strawberry | C9; D9 | −0.014; −0.013 | −0.014 | 3.8 |
| String bean | E9; F9 | −0.013; −0.014 | −0.014 | 3.8 |
| Sunflower seed | G9; H9 | −0.012; −0.013 | −0.013 | 3.8 |
| Sweet potato | A10; B10 | 0.001; −0.011 | −0.005 | 4.0 |
| Swiss cheese | C10; D10 | 1.376; 1.300 | 1.338 | 35.7 |
| Tea, black | E10; F10 | 0.229; 0.191 | 0.210 | 9.1 |
| Tomato | G10; H10 | 0.001; 0.012 | 0.007 | 4.3 |
| Trout | A11; B11 | 0.154; 0.215 | 0.185 | 8.5 |
| Tuna | C11; D11 | −0.013; 1.149 | 0.568 | 17.5 |
| Turkey | E11; F11 | 1.259; −0.013 | 0.623 | 18.8 |
| Walnut, black | G11; H11 | −0.004; 0.020 | 0.008 | 4.3 |
| Wheat | A12; B12 | −0.010; −0.012 | −0.011 | 3.8 |
| Yeast, Baker's | C12; D12 | 1.228; 1.321 | 1.274 | 34.2 |
| Yeast, Brewer's | E12; F12 | 1.132; 1.156 | 1.144 | 31.1 |
| Yogurt | G12; H12 | −0.012; −0.015 | −0.014 | 3.8 |

Table 19 shows a compilation of optical density and concentration values for 88 dietary antigens in a healthy control. The antibodies that were tested were IgM. The location specifies the location of the antigen on the test strip. For the data shown in Table 19, two sets of 12 strips were used; each set had its own calibration strip to generate a calibration graph. Each antigen is tested in two wells and the data are averaged from the readings from the two wells. The concentration readings were extrapolated from the average optical density readings and a calibration curve, as shown in FIGS. 7 and 8. FIG. 7 is used to extrapolate data from almond to lima bean in Table 19; FIG. 8 is used to extrapolate data from lobster to yogurt in Table 19. Data from Table 19 indicates that a healthy control shows salivary IgM antibody levels against buckwheat, cantaloupe, cola nut, cottage cheese, halibut, lettuce, and olive being between about 10–15 U/ml; mustard seed, scallop, strawberry, trout, and yogurt being between about 15–23 U/ml; and no foods being over about 25 U/ml.

TABLE 19

Optical Density and Concentration of Food Specific IgM in Healthy Control

| Sample | Location | OD (data) | OD (mean) | Concentration (U/ml) |
|---|---|---|---|---|
| Almond | A2; B2 | −0.005; −0.004 | −0.004 | 2.0 |
| American cheese | C2; D2 | 0.346; 0.371 | 0.358 | 10.1 |
| Apple | E2; F2 | −0.005; −0.003 | −0.004 | 2.1 |
| Avocado | G2; H2 | −0.003; −0.002 | −0.003 | 2.1 |
| Banana | A3; B3 | −0.003; −0.004 | −0.004 | 2.1 |

TABLE 19-continued

Optical Density and Concentration of Food Specific IgM in Healthy Control

| Sample | Location | OD (data) | OD (mean) | Concentration (U/ml) |
|---|---|---|---|---|
| Barley | C3; D3 | −0.004; −0.003 | −0.003 | 2.1 |
| Beef | E3; F3 | −0.002; −0.002 | −0.002 | 2.1 |
| Blueberry | G3; H3 | −0.004; 0.002 | −0.001 | 2.1 |
| Broccoli | A4; B4 | −0.003; −0.001 | −0.002 | 2.1 |
| Buckwheat | C4; D4 | 0.527; 0.534 | 0.531 | 13.9 |
| Butter | E4; F4 | −0.003; 0.148 | 0.072 | 3.7 |
| Cabbage | G4; H4 | 0.181; −0.003 | 0.089 | 4.1 |
| Cantaloupe | A5; B5 | 0.426; 0.427 | 0.427 | 11.6 |
| Carrot | C5; D5 | −0.011; 0.001 | −0.005 | 2.0 |
| Cashew | E5; F5 | −0.004; −0.003 | −0.004 | 2.1 |
| Cauliflower | G5; H5 | −0.001; −0.004 | −0.002 | 2.1 |
| Celery | A6; B6 | −0.001; −0.003 | −0.002 | 2.1 |
| Cheddar cheese | C6; D6 | 0.010; 0.000 | 0.005 | 2.2 |
| Chicken | E6; F6 | −0.001; 0.002 | 0.000 | 2.1 |
| Chili powder | G6; H6 | −0.006; 0.000 | −0.003 | 2.1 |
| Chocolate | A7; B7 | −0.006; −0.003 | −0.004 | 2.0 |
| Cinnamon | C7; D7 | −0.003; −0.002 | −0.002 | 2.1 |
| Clam | E7; F7 | 0.157; 0.175 | 0.166 | 5.8 |
| Codfish | G7; H7 | −0.002; 0.003 | 0.001 | 2.2 |
| Coffee | A8; B8 | 0.002; 0.015 | 0.009 | 2.3 |
| Cola nut | C8; D8 | 0.343; 0.402 | 0.372 | 10.4 |
| Corn | E8; F8 | 0.000; −0.002 | −0.001 | 2.1 |
| Cottage cheese | G8; H8 | 0.448; 0.410 | 0.429 | 11.6 |
| Cow's milk | A9; B9 | −0.006; −0.004 | −0.005 | 2.0 |
| Crab | C9; D9 | −0.002; 0.002 | 0.000 | 2.1 |
| Cucumber | E9; F9 | −0.003; −0.001 | −0.002 | 2.1 |
| Egg | G9; H9 | −0.002; −0.003 | −0.003 | 2.1 |
| Eggplant | A10; B10 | 0.003; 0.014 | 0.008 | 2.3 |
| Garlic | C10; D10 | 0.318; 0.221 | 0.269 | 8.1 |
| Goat's milk | E10; F10 | 0.016; 0.004 | 0.010 | 2.4 |
| Grape | G10; H10 | 0.010; 0.000 | 0.005 | 2.2 |
| Grapefruit | A11; B11 | −0.006; −0.003 | −0.004 | 2.0 |
| Green pea | C11; D11 | −0.003; −0.002 | −0.002 | 2.1 |
| Green pepper | E11; F11 | −0.001; −0.003 | −0.002 | 2.1 |
| Halibut | G11; H11 | 0.426; 0.391 | 0.408 | 11.2 |
| Honey | A12; B12 | −0.003; −0.003 | −0.003 | 2.1 |
| Lettuce, iceberg | C12; D12 | 0.511; 0.385 | 0.448 | 12.1 |
| Lemon | E12; F12 | 0.000; −0.004 | −0.002 | 2.1 |
| Lima bean | G12; H12 | −0.003; −0.003 | −0.003 | 2.1 |
| Lobster | A2; B2 | −0.004; −0.004 | −0.004 | 2.2 |
| Malt | C2; D2 | −0.003; −0.003 | −0.003 | 2.2 |
| Millet | E2; F2 | −0.005; −0.003 | −0.004 | 2.2 |
| Mushroom | G2; H2 | −0.001; −0.003 | −0.002 | 2.3 |
| Mustard seed | A3; B3 | 0.687; 0.576 | 0.631 | 16.2 |
| Oat | C3; D3 | 0.302; 0.353 | 0.328 | 9.5 |
| Olive | E3; F3 | 0.615; 0.528 | 0.572 | 14.9 |
| Onion | G3; H3 | −0.004; −0.003 | −0.004 | 2.2 |
| Orange | A4; B4 | −0.005; −0.005 | −0.005 | 2.2 |
| Oyster | C4; D4 | −0.004; −0.005 | −0.004 | 2.2 |
| Parsley | E4; F4 | −0.004; −0.005 | −0.004 | 2.2 |
| Peach | G4; H4 | −0.003; −0.002 | −0.003 | 2.3 |
| Peanut | A5; B5 | 0.140; 0.111 | 0.125 | 5.1 |
| Pinto bean | C5; D5 | −0.001; −0.001 | −0.001 | 2.3 |
| Pineapple | E5; F5 | 0.976; 0.846 | 0.911 | 22.4 |
| Pork | G5; H5 | −0.003; 0.012 | 0.004 | 2.4 |
| Potato | A6; B6 | −0.005; −0.006 | −0.006 | 2.2 |
| Rice | C6; D6 | −0.005; 0.000 | −0.003 | 2.3 |
| Rye | E6; F6 | −0.001; −0.001 | −0.001 | 2.3 |
| Safflower seed | G6; H6 | 0.135; 0.103 | 0.119 | 4.9 |
| Salmon | A7; B7 | 0.331; 0.304 | 0.318 | 9.4 |
| Sardine | C7; D7 | −0.005; −0.004 | −0.004 | 2.2 |
| Scallop | E7; F7 | 0.666; 0.559 | 0.613 | 15.8 |
| Sesame | G7; H7 | −0.004; −0.003 | −0.003 | 2.2 |
| Shrimp | A8; B8 | −0.001; 0.003 | 0.001 | 2.3 |
| Sole | C8; D8 | 0.002; 0.000 | 0.001 | 2.3 |
| Soybean | E8; F8 | 0.009; 0.006 | 0.007 | 2.5 |
| Spinach | G8; H8 | 0.227; 0.167 | 0.197 | 6.7 |
| Squash | A9; B9 | −0.004; −0.004 | −0.004 | 2.2 |
| Strawberry | C9; D9 | 0.931; 0.933 | 0.932 | 22.8 |
| String bean | E9; F9 | −0.004; −0.005 | −0.005 | 2.2 |
| Sunflower seed | G9; H9 | −0.003; −0.004 | −0.004 | 2.2 |
| Sweet potato | A10; B10 | 0.009; −0.001 | 0.004 | 2.4 |
| Swiss cheese | C10; D10 | 0.032; 0.004 | 0.018 | 2.7 |
| Tea, black | E10; F10 | 0.237; 0.205 | 0.221 | 7.2 |
| Tomato | G10; H10 | 0.011; 0.023 | 0.017 | 2.7 |
| Trout | A11; B11 | 0.864; 0.861 | 0.863 | 21.3 |
| Tuna | C11; D11 | −0.004; 0.295 | 0.146 | 5.5 |
| Turkey | E11; F11 | 0.452; −0.004 | 0.224 | 7.2 |
| Walnut, black | G11; H11 | 0.004; 0.028 | 0.016 | 2.7 |
| Wheat | A12; B12 | −0.001; −0.003 | −0.002 | 2.3 |
| Yeast, Baker's | C12; D12 | −0.007; 0.530 | 0.262 | 8.1 |
| Yeast, Brewer's | E12; F12 | 0.523; −0.003 | 0.260 | 8.0 |
| Yogurt | G12; H12 | 0.915; 0.670 | 0.792 | 19.8 |

Table 20 shows a compilation of optical density and concentration values for 88 dietary antigens in a patient with moderate food allergy and food intolerance. The antibodies that were tested were IgM. The location specifies the location of the antigen on the test strip. For the data shown in Table 20, two sets of 12 strips were used; each set had its own calibration strip to generate a calibration graph. Each antigen is tested in two wells and the data are averaged from the readings from the two wells. The concentration readings were extrapolated from the average optical density readings and a calibration curve, as shown in FIGS. 9 and 10. FIG. 9 is used to extrapolate data from almond to lima bean in Table 20; FIG. 10 is used to extrapolate data from lobster to yogurt in Table 20. Data from Table 20 indicates that a certain patient with moderate food allergy and food intolerance shows salivary IgM antibody levels against American cheese, cantaloupe, cottage cheese, lettuce, mustard, pineapple, strawberry, trout, and yogurt at above about 18 U/ml.

TABLE 20

Optical Density and Concentration of Food Specific IgM in Patient with Moderate Food Allergy and Food Intolerance

| Sample | Location | OD (data) | OD (mean) | Concentration (U/ml) |
|---|---|---|---|---|
| Almond | A2; B2 | −0.007; −0.006 | −0.007 | 2.1 |
| American cheese | C2; D2 | 1.010; 1.010 | 1.010 | 24.5 |
| Apple | E2; F2 | −0.006; −0.004 | −0.005 | 2.2 |
| Avocado | G2; H2 | −0.004; −0.004 | −0.004 | 2.2 |
| Banana | A3; B3 | −0.005; −0.006 | −0.006 | 2.1 |
| Barley | C3; D3 | −0.006; −0.005 | −0.006 | 2.1 |
| Beef | E3; F3 | −0.004; −0.004 | −0.004 | 2.2 |
| Blueberry | G3; H3 | −0.006; −0.001 | −0.003 | 2.2 |
| Broccoli | A4; B4 | −0.005; −0.003 | −0.004 | 2.2 |
| Buckwheat | C4; D4 | −0.007; −0.005 | −0.006 | 2.1 |
| Butter | E4; F4 | −0.005; −0.006 | −0.006 | 2.1 |
| Cabbage | G4; H4 | −0.006; −0.006 | −0.006 | 2.1 |
| Cantaloupe | A5; B5 | 0.684; 0.767 | 0.725 | 18.2 |
| Carrot | C5; D5 | −0.006; −0.002 | −0.004 | 2.2 |
| Cashew | E5; F5 | −0.006; −0.007 | −0.006 | 2.1 |
| Cauliflower | G5; H5 | −0.004; −0.005 | −0.005 | 2.2 |
| Celery | A6; B6 | −0.004; −0.006 | −0.005 | 2.1 |
| Cheddar cheese | C6; D6 | −0.006; −0.002 | −0.004 | 2.2 |
| Chicken | E6; F6 | −0.001; 0.001 | 0.000 | 2.2 |
| Chili powder | G6; H6 | −0.005; −0.002 | −0.003 | 2.2 |
| Chocolate | A7; B7 | −0.003; −0.005 | −0.004 | 2.2 |
| Cinnamon | C7; D7 | −0.005; −0.004 | −0.004 | 2.2 |
| Clam | E7; F7 | 0.429; 0.472 | 0.451 | 12.2 |
| Codfish | G7; H7 | −0.004; 0.002 | −0.001 | 2.2 |
| Coffee | A8; B8 | 0.001; 0.015 | 0.008 | 2.4 |
| Cola nut | C8; D8 | 0.006; −0.001 | 0.002 | 2.3 |
| Corn | E8; F8 | 0.003; −0.001 | 0.001 | 2.3 |

TABLE 20-continued

Optical Density and Concentration of Food Specific IgM
in Patient with Moderate Food Allergy and Food Intolerance

| Sample | Location | OD (data) | OD (mean) | Concentration (U/ml) |
|---|---|---|---|---|
| Cottage cheese | G8; H8 | 0.813; 0.745 | 0.779 | 19.4 |
| Cow's milk | A9; B9 | −0.005; −0.006 | −0.005 | 2.1 |
| Crab | C9; D9 | −0.004; 0.001 | −0.002 | 2.2 |
| Cucumber | E9; F9 | −0.006; −0.003 | −0.004 | 2.2 |
| Egg | G9; H9 | −0.004; −0.005 | −0.005 | 2.1 |
| Eggplant | A10; B10 | 0.002; 0.013 | 0.007 | 2.4 |
| Garlic | C10; D10 | 0.011; 0.001 | 0.006 | 2.4 |
| Goat's milk | E10; F10 | 0.015; 0.002 | 0.008 | 2.4 |
| Grape | G10; H10 | 0.011; −0.002 | 0.005 | 2.4 |
| Grapefruit | A11; B11 | −0.008; −0.005 | −0.006 | 2.1 |
| Green pea | C11; D11 | −0.005; −0.004 | −0.005 | 2.2 |
| Green pepper | E11; F11 | −0.003; −0.005 | −0.004 | 2.2 |
| Halibut | G11; H11 | −0.004; −0.002 | −0.003 | 2.2 |
| Honey | A12; B12 | −0.005; −0.005 | −0.005 | 2.1 |
| Lettuce, iceberg | C12; D12 | 0.855; 0.686 | 0.770 | 19.2 |
| Lemon | E12; F12 | −0.002; −0.006 | −0.004 | 2.2 |
| Lima bean | G12; H12 | −0.004; −0.005 | −0.004 | 2.2 |
| Lobster | A2; B2 | 0.002; 0.001 | 0.001 | 2.2 |
| Malt | C2; D2 | 0.002; 0.002 | 0.002 | 2.3 |
| Millet | E2; F2 | 0.000; 0.003 | 0.002 | 2.3 |
| Mushroom | G2; H2 | 0.004; 0.002 | 0.003 | 2.3 |
| Mustard seed | A3; B3 | 0.999; 0.849 | 0.924 | 22.6 |
| Oat | C3; D3 | 0.001; 0.001 | 0.001 | 2.2 |
| Olive | E3; F3 | 0.554; 0.474 | 0.514 | 13.6 |
| Onion | G3; H3 | 0.001; 0.003 | 0.002 | 2.3 |
| Orange | A4; B4 | 0.000; 0.000 | 0.000 | 2.2 |
| Oyster | C4; D4 | 0.002; 0.001 | 0.001 | 2.2 |
| Parsley | E4; F4 | 0.001; 0.001 | 0.001 | 2.2 |
| Peach | G4; H4 | 0.002; 0.003 | 0.003 | 2.3 |
| Peanut | A5; B5 | 0.147; 0.117 | 0.132 | 5.1 |
| Pinto bean | C5; D5 | 0.005; 0.005 | 0.005 | 2.3 |
| Pineapple | E5; F5 | 1.555; 0.132 | 1.444 | 34.1 |
| Pork | G5; H5 | 0.003; 0.018 | 0.010 | 2.4 |
| Potato | A6; B6 | 0.000; 0.000 | 0.000 | 2.2 |
| Rice | C6; D6 | 0.001; 0.005 | 0.003 | 2.3 |
| Rye | E6; F6 | 0.005; 0.004 | 0.005 | 2.3 |
| Safflower seed | G6; H6 | 0.006; 0.001 | 0.003 | 2.3 |
| Salmon | A7; B7 | −0.001; 0.001 | 0.000 | 2.2 |
| Sardine | C7; D7 | 0.001; 0.001 | 0.001 | 2.2 |
| Scallop | E7; F7 | 0.003; 0.003 | 0.003 | 2.3 |
| Sesame | G7; H7 | 0.001; 0.002 | 0.002 | 2.3 |
| Shrimp | A8; B8 | 0.004; 0.009 | 0.007 | 2.4 |
| Sole | C8; D8 | 0.007; 0.006 | 0.006 | 2.4 |
| Soybean | E8; F8 | 0.015; 0.011 | 0.013 | 2.5 |
| Spinach | G8; H8 | 0.440; 0.346 | 0.393 | 10.9 |
| Squash | A9; B9 | 0.001; 0.002 | 0.002 | 2.3 |
| Strawberry | C9; D9 | 1.341; 1.436 | 1.389 | 32.9 |
| String bean | E9; F9 | 0.002; 0.001 | 0.001 | 2.2 |
| Sunflower seed | G9; H9 | 0.003; 0.002 | 0.002 | 2.3 |
| Sweet potato | A10; B10 | 0.014; 0.003 | 0.009 | 2.4 |
| Swiss cheese | C10; D10 | 0.037; 0.010 | 0.023 | 2.7 |
| Tea, black | E10; F10 | 0.242; 0.212 | 0.227 | 7.2 |
| Tomato | G10; H10 | 0.017; 0.029 | 0.023 | 2.7 |
| Trout | A11; B11 | 1.301; 1.261 | 1.281 | 30.5 |
| Tuna | C11; D11 | 0.001; 0.002 | 0.002 | 2.3 |
| Turkey | E11; F11 | 0.002; 0.001 | 0.002 | 2.3 |
| Walnut, black | G11; H11 | 0.009; 0.020 | 0.014 | 2.5 |
| Wheat | A12; B12 | 0.005; 0.002 | 0.004 | 2.3 |
| Yeast, Baker's | C12; D12 | 0.000; 0.001 | 0.001 | 2.2 |
| Yeast, Brewer's | E12; F12 | 0.002; 0.002 | 0.002 | 2.3 |
| Yogurt | G12; H12 | 1.403; 1.180 | 1.291 | 30.7 |

Table 21 shows a compilation of optical density and concentration values for 88 dietary antigens in a patient with severe food allergy and food intolerance. The antibodies that were tested were IgM. The location specifies the location of the antigen on the test strip. For the data shown in Table 21, two sets of 12 strips were used; each set had its own calibration strip to generate a calibration graph. Each antigen is tested in two wells and the data are averaged from the readings from the two wells. The concentration readings were extrapolated from the average optical density readings and a calibration curve, as shown in FIGS. 11 and 12. FIG. 11 is used to extrapolate data from almond to lima bean in Table 21; FIG. 12 is used to extrapolate data from lobster to yogurt in Table 21. Data from Table 21 indicates that a certain patient with severe food allergy and food intolerance shows salivary IgM antibody levels against avocado, cashew, celery, chili powder, coffee, corn, garlic, lettuce, lemon, millet, mustard seed, onion, peanut, pork, rice, sesame, sole, squash, string beans, tomato, trout, walnut, and Baker's yeast at above about 20 U/ml.

TABLE 21

Optical Density and Concentration of Food Specific IgM in
Patient with Severe Food Allergy and Food Intolerance

| Sample | Location | OD (data) | OD (mean) | Concentration (U/ml) |
|---|---|---|---|---|
| Almond | A2; B2 | −0.010; −0.012 | −0.011 | 3.7 |
| American cheese | C2; D2 | 0.495; 0.568 | 0.532 | 16.7 |
| Apple | E2; F2 | −0.012; −0.010 | −0.011 | 3.7 |
| Avocado | G2; H2 | 1.532; 1.493 | 1.513 | 40.1 |
| Banana | A3; B3 | 0.422; 0.355 | 0.389 | 13.3 |
| Barley | C3; D3 | −0.011; −0.014 | −0.013 | 3.7 |
| Beef | E3; F3 | −0.012; −0.008 | −0.010 | 3.8 |
| Blueberry | G3; H3 | −0.012; −0.010 | −0.011 | 3.7 |
| Broccoli | A4; B4 | −0.012; −0.013 | −0.013 | 3.7 |
| Buckwheat | C4; D4 | −0.011; −0.012 | −0.012 | 3.7 |
| Butter | E4; F4 | 0.545; 0.489 | 0.517 | 16.4 |
| Cabbage | G4; H4 | −0.010; −0.004 | −0.007 | 3.8 |
| Cantaloupe | A5; B5 | 0.076; 0.054 | 0.065 | 5.6 |
| Carrot | C5; D5 | −0.008; −0.008 | −0.008 | 3.8 |
| Cashew | E5; F5 | 1.851; 1.902 | 1.877 | 48.8 |
| Cauliflower | G5; H5 | −0.010; 0.002 | −0.004 | 3.9 |
| Celery | A6; B6 | 0.730; 0.748 | 0.739 | 21.7 |
| Cheddar cheese | C6; D6 | −0.012; −0.007 | −0.010 | 3.8 |
| Chicken | E6; F6 | −0.010; −0.008 | −0.009 | 3.8 |
| Chili powder | G6; H6 | 0.884; 0.971 | 0.927 | 26.2 |
| Chocolate | A7; B7 | −0.018; −0.011 | −0.014 | 3.7 |
| Cinnamon | C7; D7 | −0.012; −0.012 | −0.012 | 3.7 |
| Clam | E7; F7 | −0.013; −0.007 | −0.010 | 3.8 |
| Codfish | G7; H7 | −0.011; −0.010 | −0.011 | 3.8 |
| Coffee | A8; B8 | 1.651; 1.726 | 1.688 | 44.3 |
| Cola nut | C8; D8 | −0.005; −0.010 | −0.007 | 3.8 |
| Corn | E8; F8 | 1.051; 1.516 | 1.283 | 34.7 |
| Cottage cheese | G8; H8 | 0.208; 0.150 | 0.179 | 8.3 |
| Cow's milk | A9; B9 | −0.012; −0.012 | −0.012 | 3.7 |
| Crab | C9; D9 | −0.013; −0.012 | −0.012 | 3.7 |
| Cucumber | E9; F9 | −0.012; −0.013 | −0.012 | 3.7 |
| Egg | G9; H9 | −0.011; −0.011 | −0.011 | 3.7 |
| Eggplant | A10; B10 | 0.001; −0.010 | −0.004 | 3.9 |
| Garlic | C10; D10 | 1.358; 1.280 | 1.319 | 35.5 |
| Goat's milk | E10; F10 | 0.230; 0.189 | 0.210 | 9.0 |
| Grape | G10; H10 | 0.003; 0.015 | 0.009 | 4.2 |
| Grapefruit | A11; B11 | 0.156; 0.218 | 0.187 | 8.5 |
| Green pea | C11; D11 | −0.012; 1.134 | 0.561 | 17.4 |
| Green pepper | E11; F11 | 1.244; −0.011 | 0.616 | 18.7 |
| Halibut | G11; H11 | −0.002; 0.020 | 0.009 | 4.2 |
| Honey | A12; B12 | −0.009; −0.011 | −0.010 | 3.8 |
| Lettuce, iceberg | C12; D12 | 1.212; 1.304 | 1.258 | 34.0 |
| Lemon | E12; F12 | 1.119; 1.147 | 1.133 | 31.1 |
| Lima bean | G12; H12 | −0.011; −0.014 | −0.012 | 3.7 |
| Lobster | A2; B2 | −0.072; −0.074 | −0.073 | 3.0 |
| Malt | C2; D2 | −0.066; −0.064 | −0.065 | 3.3 |
| Millet | E2; F2 | 1.327; 1.198 | 1.262 | 38.6 |
| Mushroom | G2; H2 | −0.070; −0.075 | −0.073 | 3.1 |
| Mustard seed | A3; B3 | 1.415; 1.317 | 1.366 | 41.3 |
| Oat | C3; D3 | −0.072; −0.069 | −0.070 | 3.1 |
| Olive | E3; F3 | −0.071; −0.072 | −0.072 | 3.1 |
| Onion | G3; H3 | 0.646; 0.611 | 0.628 | 21.7 |
| Orange | A4; B4 | −0.069; −0.063 | −0.066 | 3.2 |
| Oyster | C4; D4 | 0.344; 0.355 | 0.349 | 14.3 |
| Parsley | E4; F4 | −0.068; −0.068 | −0.068 | 3.2 |
| Peach | G4; H4 | −0.058; −0.067 | −0.062 | 3.3 |
| Peanut | A5; B5 | 1.222; 1.143 | 1.182 | 36.4 |
| Pinto bean | C5; D5 | −0.065; −0.071 | −0.068 | 3.2 |
| Pineapple | E5; F5 | −0.065; −0.064 | −0.064 | 3.3 |

TABLE 21-continued

Optical Density and Concentration of Food Specific IgM in Patient with Severe Food Allergy and Food Intolerance

| Sample | Location | OD (data) | OD (mean) | Concentration (U/ml) |
|---|---|---|---|---|
| Pork | G5; H5 | 1.068; 1.260 | 1.164 | 35.9 |
| Potato | A6; B6 | −0.068; −0.072 | −0.070 | 3.1 |
| Rice | C6; D6 | 1.088; 1.019 | 1.053 | 33.0 |
| Rye | E6; F6 | −0.069; −0.068 | −0.069 | 3.2 |
| Safflower seed | G6; H6 | −0.057; −0.060 | −0.059 | 3.4 |
| Salmon | A7; B7 | −0.071; −0.066 | −0.068 | 3.2 |
| Sardine | C7; D7 | −0.071; −0.069 | −0.070 | 3.1 |
| Scallop | E7; F7 | −0.065; −0.072 | −0.068 | 3.2 |
| Sesame | G7; H7 | 0.758; 0.790 | 0.774 | 25.6 |
| Shrimp | A8; B8 | −0.072; −0.069 | −0.071 | 3.1 |
| Sole | C8; D8 | 0.750; 0.914 | 0.832 | 27.1 |
| Soybean | E8; F8 | −0.064; −0.067 | −0.066 | 3.2 |
| Spinach | G8; H8 | −0.065; −0.061 | −0.063 | 3.3 |
| Squash | A9; B9 | 0.680; 0.742 | 0.711 | 23.9 |
| Strawberry | C9; D9 | −0.069; −0.070 | −0.069 | 3.2 |
| String bean | E9; F9 | 0.585; 0.553 | 0.569 | 20.1 |
| Sunflower seed | G9; H9 | −0.068; −0.072 | −0.070 | 3.1 |
| Sweet potato | A10; B10 | −0.073; −0.075 | −0.074 | 3.0 |
| Swiss cheese | C10; D10 | −0.075; −0.069 | −0.072 | 3.1 |
| Tea, black | E10; F10 | −0.067; −0.065 | −0.066 | 3.2 |
| Tomato | G10; H10 | 0.850; 0.940 | 0.895 | 28.8 |
| Trout | A11; B11 | 0.816; 0.907 | 0.861 | 27.9 |
| Tuna | C11; D11 | −0.072; −0.062 | −0.067 | 3.2 |
| Turkey | E11; F11 | −0.064; −0.058 | −0.061 | 3.4 |
| Walnut, black | G11; H11 | 0.531; 0.604 | 0.567 | 20.1 |
| Wheat | A12; B12 | −0.073; −0.075 | −0.074 | 3.0 |
| Yeast, Baker's | C12; D12 | 1.385; 0.833 | 1.109 | 34.5 |
| Yeast, Brewer's | E12; F12 | −0.073; −0.070 | −0.071 | 3.1 |
| Yogurt | G12; H12 | −0.069; −0.071 | −0.070 | 3.1 |

The above tables show that a patient with moderate or severe food allergy or food intolerance generally higher antibody measurements against dietary antigens than healthy controls. To summarize the results of this Example, we present the following statistics.

For a healthy control, the salivary IgA antibody levels are generally below about 10 U/ml; only two salivary IgA antibody level readings were above about 10 U/ml. The salivary IgM antibody levels are generally below about 10 U/ml; seven salivary IgM antibody level readings were between about 10 and 15 U/ml; five salivary IgM antibody level readings were between about 15 and 23 U/ml.

For a patient with moderate food allergy and food intolerance, the salivary IgA antibody levels are generally below about 15 U/ml; nine salivary IgA antibody level readings were above about 15 U/ml. The salivary IgM antibody levels are generally below about 18 U/ml; nine salivary IgM antibody level readings were above about 18 U/ml.

For a patient with severe food allergy and food intolerance, the salivary IgA antibody levels are generally below about 20 U/ml; twenty salivary IgA antibody level readings were above about 20 U/ml. The salivary IgM antibody levels are generally below about 20 U/ml; twenty-three salivary IgM antibody level readings were above about 20 U/ml.

The results of the test panels should be examined as panels. For example, most of the readings for the salivary IgA antibody levels in the healthy control are under about 10 U/ml. Likewise, most of the readings for the salivary IgM antibody levels in the healthy control are under about 10 U/ml. However, there are certain readings in the panel of the healthy control that are higher than about 10 U/ml. Particularly higher readings in the healthy control may indicate sensitivity to the corresponding dietary antigen. For example, in Table 16, readings for salivary IgA antibody levels for banana and beef were over about 10 U/ml; thus, these reading may indicate sensitivities to banana and beef in the healthy control. In the example of the readings for salivary IgA antibody levels, if 10 U/ml were taken to be the baseline measurement, then eighty-six of the eighty-eight readings are below the baseline, or 98% of the readings are below the baseline. In the example of the readings for salivary IgM antibody levels, if 10 U/ml were taken to be the baseline measurement, then seventy-four of the eighty-eight readings are below the baseline, or 84% of the readings are below the baseline.

The readings of salivary antibody levels to the dietary antigens of patients with moderate and severe food allergy and food intolerance are generally higher than the readings of the healthy control. These higher readings may indicate particular food allergy and food intolerance to the corresponding dietary antigen. For example, in the patient with moderate food allergy and food intolerance, there were twelve readings for salivary IgA antibody levels that were above about 10 U/ml. In the patient with severe food allergy and food intolerance, there were twenty-nine readings for salivary IgA antibody levels that were above 10 U/ml. In contrast, as mentioned above, in the healthy control, there were two readings for salivary IgA antibody levels that were above 10 U/ml. Therefore, the person with moderate food allergy and food intolerance has more readings of salivary antibody levels to dietary antigens that are higher than baseline reading, when compared to the healthy control. The person with severe food allergy and food intolerance has more readings of salivary antibody levels to dietary antigens that are higher than baseline, when compared to the person with moderate food allergy and food intolerance or the healthy control.

The results of the test panels can allow for a faster and more accurate diagnosis of food allergy and food intolerance.

References

1. Anderson J A. The establishment of common language concerning adverse reactions to foods and food additives. *J Allergy Clin Immunol* 78:140, 1986.
2. Erikson N E. Food sensitivity reported by patients with asthma and hay fever. *Allergy* 33:189, 1978.
3. Sloan A E. A perspective on popular perceptions of adverse reactions to food. *J Allergy Clin Immunol* 78:127, 1986.
4. Sampson S A, Metcalfe D D. Immediate reactions to foods. In Metcalfe D D, Sampson H A, Simon R A, editors. *Food allergy: adverse reactions to foods and food additives*. Oxford, 1991, Blackwell Scientific Publications.
5. Kushimoto H, Aoki T: Masked type I wheat allergy. *Arch Dermatol* 121:355, 1985.
6. Businco L, Benincori N, Cantani A et al., Chronic diarrhea due to cow's milk allergy: a 4–10 year follow-up study, *Ann Allergy* 55:844, 1985.
7. Enberg R N. Food-induced oropharyngeal symptoms: the oral allergy syndrome. In Anderson J A, editor. *Food allergy: immunology and allergy clinics of North America* (vol. II), Philadelphia, 1991, W B Saunders.
8. Danneus A, Johansson S G O. A follow up study of infants with adverse reactions to cow's milk. I. Serum IgE, skin test reactions and RAST in relation to clinical course, *Acta Pediatr Scand* 68:377, 1979.
9. Kohno T, Kobashiri Y, Sugie Y, Takai S, Watabe K, Kaino Y, Kida K. Antibodies to food antigens in Japanese patients with Type-1 diabetes mellitus. *Diabetes Res Clin Pract* 55:1, 2002.
10. Kiyono H, Kweon M N, Hiroi T, Takahashi I. The mucosal immune system: from specialized immune defense to inflammation and allergy. *Acta Odntol Scand* 59:145, 2001.
11. Kanda M, Inove H, Fukuizumi T, Tsujisawa T, Tominaga K, Fukuda J. Detection and rapid increase of salivary antibodies to *Staphylococcus lentus* and indigenous bacterium in rabbit saliva, through a single tonsillar, Application of bacterial cells. *Oral Microbiol Immunol* 16:257, 2001.
12. Zee K Y, Samaranayake L P, Attstrom R. Salivary Immunoglobulin A levels in rapid and slow plaque formers: A pilot study. *Microbio S* 106 Suppl 2:81, 2001.
13. Plante M, Jones T, Allard F, Torossian K, Gauthier J, St-Félix N, White G L, Lowell G H, Burt D S. Nasal immunization with subunit proteosome influenza vaccines induces serum HAI, mucosal IgA and protection against influenza challenge. *Vaccine* 20:218, 2002.
14. Kraft S C, Rothbert R M, Kramer C M. Gastric output and circulating anti-BSA in adults. *Clin and Exp Immuno* 2:321–326, 1967.
15. Kagnoff M F. Effects of antigen feeding on intestinal and systemic immune responses. I. Priming of precursor cytotoxic T-cells by antigen feeding. *J Immunol* 120:395–399, 1978.
16. Challacombe S J, The induction of secretory IgA responses in: food allergy and intolerance edited by Brostoff J, Challacombe S J, published by W. B. Sanders Eastborne England, 1987.
17. Davies A. An investigation in to the serological properties of dysentery stools. *Lancet* 203:1009–1012, 1922.
18. Montrien B de, Serre. Etudes des immunoglobulins salivaires aptes vaccination locale antistreptococcique. *Pathol Biol* (Paris) 22:305–312, 1974.
19. McGhee J R, Michalek S M, Webb J et al., Effective immunity to dental caries: protection of gnotobiotic rats by local immunization with Streptococcus mutants. *J Immuno* 114:300–305, 1975.
20. Krasse B, Gahnberg L, Bratthall D. Antibodies reacting with Streptococcus mutants in secretion from minor salivary glands in humans. *Adv Exp Med Biol* 107:349–354, 1978.
21. Husband A M, Gowens J L. The origin and antigen-dependent distribution of IgA containing cells in the intestine. *J Exp Med* 148:1146–1160, 1978.
22. Mesenteric J, McGhee J R, Arnold R R. Selective induction of an immune response in external secretions by ingestion of bacterial antigen. *J Clin Invest* 61:731–737, 1978.
23. Walker W A, Isselbacher K J. Intestinal antibodies. *New Engl J Med* 297:767–773, 1977.
24. Clements R L. Fruit proteins: extraction and electrophoresis. *Anal Biochem* 13:390, 1965.
25. Bradford M M. A rapid and sensitive method for the quantitation of microquantities of protein utilizing the principle of protein-dye binding. *Anal Biochem* 72:248, 1976.
26. Steinhart H, Wigotzki M, Zunker K. Introducing allergists to food chemistry. *Allergy* 56: Suppl. 67:9, 2001.
27. Ortolani C, Ispano M, Scibilia J, Pastorello E A. Introducing chemists to food allergy. *Allergy* 56: Suppl 67:5, 2001.
28. Barnett D, Baldo B A, Howden M E H: Multiplicity of allergens in peanuts. *J Allergy Clin Immunol* 72:61, 1983.
29. Aas K, Jebsen J W. Studies of hypersensitivity to fish. Partial purification and crystallization of a major allergenic component of cod. *Int Arch Allergy Appl Immunol* 32:1, 1967.
30. Izumi H, Adachi T, Fuji N et al., Nucleotide sequence of a cDNA clone encoding a major allergenic protein in rice seeds. *FEBS Lett* 302:213, 1992.
31. Elsayed S, Apold J. Immunochemical analysis of codfish allergen M: locations of the immunoglobulin binding sites as demonstrated by the native and synthetic peptides. *Allergy* 38:449, 1983.
32. Nagpal S, Rajappa L, Metcalfe D D et al., Isolation and characterization of heat stable allergens from shrimp (*Panaeus inducus*), *J Allergy Clin Immunol* 83:26, 1989.
33. Chatchatee P, Järvinen K M, Bardina L, Vila L, Beyer K, Sampson H A. Identification of IgE and IgG binding epitopes of B- and K-case in cow's milk allergic patients. *Clinical Experimental Allergy* 31:1256, 2001.
34. Palosuo K, Alenius H, Varjone N E, Kalkkinen N, Reunala T. Rye γ-70 and γ-35 secalins and barley γ-3 hordein in cross-react with W-5 gliadin: a major allergen in wheat-dependent, exercise-induced anaphylaxis. *Clinical Experimental Allergy* 31:466, 2001.
35. Wal J M. Structure and function of milk allergens. *Allergy* 56: Suppl 67:35, 2001.
36. Poulsen L K, Hansen T K, Nørgaard A, Vestergaard H, Skov P S, Bindslev-Jensen C. Allergens from fish and egg. *Allergy* 56: Suppl 67:39. 2001.
37. Vieth S S, Scheurer S, Reindl J, Lüttkopf D, Wangorsch A, Kästner M, Haase T, Haustein D. Optimized allergen extracts and recombinant allergens in diagnostic applications. *Allergy* 56: Suppl 67:78, 2001.
38. Leung P S C, Chu K H. cDNA cloning and molecular identification of the major oyster allergen from the pacific oyster crassostrea gigas. *Clinical and Experimental Allergy* 31:1287, 2001.

What is claimed is:

1. A method for determining a presence of food allergy or food intolerance to a food in a patient, comprising:
 (a) determining a level of antibodies against a dietary antigen present in the food in a saliva sample from said patient;
 (b) comparing the level determined in step (a) with normal levels of said antibodies in said saliva sample, wherein
  (i) lower than normal levels or about normal levels of dietary antigen antibodies indicate optimal conditions;
  (ii) higher than normal levels of dietary antigen antibodies indicate a food allergy or food intolerance to the food.

2. The method according to claim 1, wherein the level of antibodies is determined by the antibodies' ability to bind to a recombinant antigen, a synthetic peptide, a peptide prepared by enzymatic digestion corresponding to said dietary antigen, or a cross-reactive tissue antigen.

3. The method according to claim 1, wherein the normal levels of antibodies is determined by a baseline measurement of antibodies against dietary antigens for individuals without symptoms relating to food allergy or food intolerance.

4. The method according to claim 1, wherein the dietary antigen is obtained from a food category selected from the group consisting of milk and products thereof; eggs and products thereof; meat and products thereof; fish, mollusks, and crustaceans and products thereof; oils, fats, and products thereof; grains and products thereof; pulses, seeds, kernels, nuts, and products thereof vegetables and products thereof fruits and products thereof; sugar, sugar products, chocolate products, and confectionary; and spices and herbs.

5. The method according to claim 4, wherein the milk and products thereof is selected from American cheese, cheddar cheese, cottage cheese, cow's milk, goat's milk, Swiss cheese, or yogurt.

6. The method according to claim 4, wherein the eggs and products thereof is egg.

7. The method according to claim 4, wherein the meat and products thereof is selected from beef, chicken, pork, or turkey.

8. The method according to claim 4, wherein the fish, mollusks, and crustaceans and products thereof is selected from clam, codfish, crab, halibut, lobster, oyster, salmon, sardine, scallop, shrimp, sole, trout, or tuna.

9. The method according to claim 4, wherein the oils, fats, and products thereof is butter.

10. The method according to claim 4, wherein the grains and products thereof is selected from barley, buckwheat, malt, oat, rice, rye, or wheat.

11. The method according to claim 4, wherein the pulses, seeds, kernels, nuts, and products thereof is selected from almond, cashew, coffee, cola nut, lima bean, millet, peanut, pinto bean, safflower seed, sesame, soybean, sunflower seed, or walnut.

12. The method according to claim 4, wherein the vegetables and products thereof is selected from broccoli, cabbage, carrot, cauliflower, celery, corn, cucumber, eggplant, green pea, green pepper, iceberg lettuce, mushroom, onion, potato, spinach, squash, string bean, sweet potato, or tomato.

13. The method according to claim 4, wherein the fruits and products thereof is selected from apple, avocado, banana, blueberry, cantaloupe, grape, grapefruit, lemon, olive, orange, peach, pineapple, or strawberry.

14. The method according to claim 4, wherein the sugar, sugar products, chocolate products, and confectionary is selected from chocolate, honey, or cane sugar.

15. The method according to claim 4, wherein the spices and herbs is selected from chili powder, cinnamon, garlic, mustard seed, parsley, tea, or yeast.

16. The method according to claim 1, wherein determining the level of antibodies is accomplished using an immunoassay.

17. The method according to claim 16, wherein the immunoassay is an ELISA test, RIA test, latex agglutination, beads assay, or a proteomic assay.

18. The method according to claim 16, wherein the immunoassay is an ELISA test.

19. The method according to claim 1, wherein the antibodies are selected from the group consisting of IgA and IgM.

20. A method for determining a type of antibody in a presence of allergy or intolerance to a food in a patient, comprising:
   (a) determining a level of antibodies against a dietary antigen present in the food in a first mucosal sample from said patient;
   (b) determining a level of antibodies against cross-reactive tissue antigen present in a second muscosal sample from said patient, wherein said first and second samples are the same or different; and
   (c) comparing the level of antibodies determined in steps a) and b) with normal levels of said antibodies, wherein
      (i) about normal levels of antibodies against the dietary antigen and normal levels of antibodies against cross-reactive tissue antigen indicate optimal conditions;
      (ii) higher than normal levels of antibodies against the dietary antigen and about normal levels of antibodies against cross-reactive tissue antigen indicate food allergy and intolerance without cross-reacting to tissue antigens;
      (iii) about normal levels of antibodies against the dietary antigen and higher than normal levels of antibodies against cross-reactive tissue antigen indicate an autoimmune reaction not related to the dietary antigens; and
      (iv) higher than normal levels of antibodies against the dietary antigen and higher than normal levels of antibodies against cross-reactive tissue antigen indicate a presence of food allergy and intolerance resulting in an autoimmune reaction.

21. The method according to claim 20, wherein the cross-reactive tissue antigen is selected from the group consisting of lectin, lectin receptor, tropomyosin, smooth muscle, epithelial cell antigen, enzyme, cytochrome P-450 enzyme, and transglutaminase.

* * * * *

UNITED STATES PATENT AND TRADEMARK OFFICE
CERTIFICATE OF CORRECTION

PATENT NO. : 6,858,398 B2
DATED : February 22, 2005
INVENTOR(S) : Aristo Vojdani It is certified that error appears in the above-identified patent and that said Letters Patent is hereby corrected as shown below:

Title page,
Item [56], References Cited, OTHER PUBLICATIONS,
"A. E. Sloan et al.," reference, after "78," delete "$^{TM}$1" and insert -- #1 --; also
"J. R. McGhee, et al.," reference, delete "mutants," and insert -- Mutans, --.

Column 26,
Line 63, insert -- ; -- before "vegetables"; also after "vegetables and products thereof" insert -- ; --.

Signed and Sealed this

Fourth Day of April, 2006

JON W. DUDAS
*Director of the United States Patent and Trademark Office*